(12) United States Patent
Ono

(10) Patent No.: US 8,823,789 B2
(45) Date of Patent: Sep. 2, 2014

(54) IMAGING APPARATUS

(71) Applicant: Olympus Medical Systems Corp., Tokyo (JP)

(72) Inventor: Wataru Ono, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/757,918

(22) Filed: Feb. 4, 2013

(65) Prior Publication Data
US 2013/0208101 A1 Aug. 15, 2013

Related U.S. Application Data

(63) Continuation of application No. PCT/JP2012/070366, filed on Aug. 9, 2012.

(30) Foreign Application Priority Data

Aug. 15, 2011 (JP) .................................. 2011-177692

(51) Int. Cl.
| | |
|---|---|
| H04N 5/235 | (2006.01) |
| A61B 1/00 | (2006.01) |
| A61B 1/04 | (2006.01) |
| H04N 5/232 | (2006.01) |
| A61B 1/05 | (2006.01) |
| H04N 13/02 | (2006.01) |
| A61B 1/06 | (2006.01) |
| H04N 5/225 | (2006.01) |
| H04N 5/345 | (2011.01) |
| H04N 5/347 | (2011.01) |

(52) U.S. Cl.
CPC .......... *H04N 5/2353* (2013.01); *A61B 1/00193* (2013.01); *H04N 13/0239* (2013.01); *A61B 1/04* (2013.01); *A61B 1/06* (2013.01); *H04N 2005/2255* (2013.01); *A61B 1/00009* (2013.01); *H04N 5/3456* (2013.01); *H04N 5/2258* (2013.01); *H04N 5/23229* (2013.01); *H04N 5/347* (2013.01); *A61B 1/051* (2013.01)
USPC .......................................................... 348/65

(58) Field of Classification Search
CPC ................ A61B 1/00193; H04N 5/272–5/353
See application file for complete search history.

(56) References Cited

U.S. PATENT DOCUMENTS

| | | | | |
|---|---|---|---|---|
| 5,751,341 A * | 5/1998 | Chaleki et al. | ................... | 348/65 |
| 6,466,268 B1 * | 10/2002 | Kato et al. | ..................... | 348/383 |
| 6,489,987 B1 * | 12/2002 | Higuchi et al. | ................. | 348/65 |

(Continued)

FOREIGN PATENT DOCUMENTS

| | | |
|---|---|---|
| JP | 6-54803 A | 3/1994 |
| JP | 11-32982 A | 2/1999 |

(Continued)

OTHER PUBLICATIONS

International Search Report PCT/JP2012/070366 dated Oct. 23, 2012.

*Primary Examiner* — William C Vaughn, Jr.
*Assistant Examiner* — Luis M Perez
(74) *Attorney, Agent, or Firm* — Scully, Scott, Murphy & Presser, P.C.

(57) ABSTRACT

An imaging apparatus includes first and second imaging units, a reading unit that reads pixel information from pixels set as a reading target in each of the first and second imaging units, a control unit that sets the pixels as the reading target in each of the first and second imaging units in a manner such that the pixel information is alternately read from the first and second imaging units by the reading unit, and controls timing of exposure processes in the first and second imaging units and timing of reading processes of the pixel information for the first and second imaging units by the reading unit, to be correlated with one another, a transmission unit that transmits the pixel information read from each of the first and second imaging units in a same transmission path, and an image processing unit that generates an image based on the pixel information.

13 Claims, 20 Drawing Sheets

(56) References Cited

U.S. PATENT DOCUMENTS

| | | | |
|---|---|---|---|
| 6,515,701 B2 * | 2/2003 | Clark et al. | 348/308 |
| 7,289,140 B2 * | 10/2007 | Kobayashi | 348/68 |
| 7,393,321 B2 * | 7/2008 | Doguchi et al. | 600/109 |
| 7,635,330 B2 * | 12/2009 | Kang et al. | 600/160 |
| 7,643,079 B2 * | 1/2010 | Oshima et al. | 348/315 |
| 7,889,228 B2 * | 2/2011 | Ishihara et al. | 348/65 |
| 8,520,796 B2 * | 8/2013 | Koyama | 377/54 |
| 2007/0153542 A1 * | 7/2007 | Gono et al. | 362/574 |
| 2009/0080175 A1 * | 3/2009 | Mizuno et al. | 362/4 |
| 2010/0069713 A1 * | 3/2010 | Endo et al. | 600/109 |
| 2011/0292258 A1 * | 12/2011 | Adler et al. | 348/263 |
| 2013/0041221 A1 * | 2/2013 | McDdwall et al. | 600/111 |

FOREIGN PATENT DOCUMENTS

| | | |
|---|---|---|
| JP | 2000-258697 A | 9/2000 |
| JP | 2010-68992 A | 4/2010 |
| JP | 2010-130570 A | 6/2010 |

\* cited by examiner

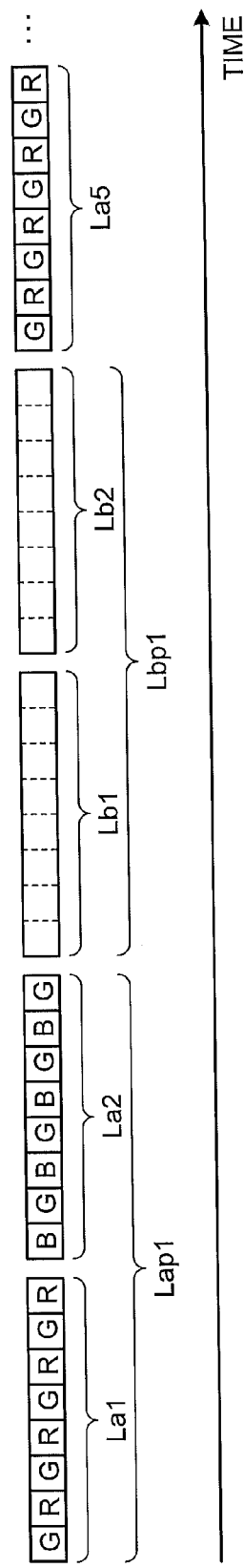

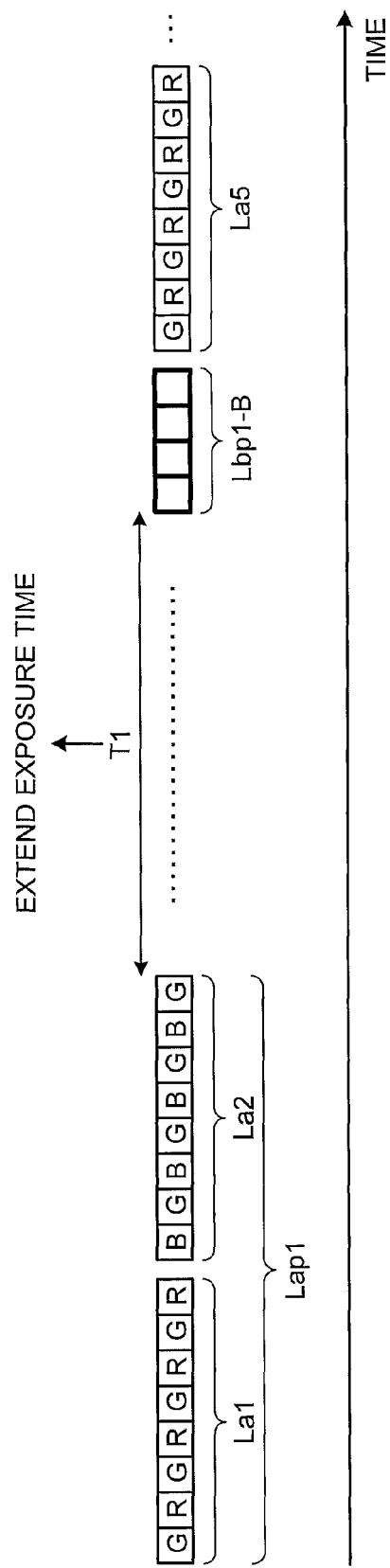

FIG.10A

|   |   |   |   |   |   |   |   |   |
|---|---|---|---|---|---|---|---|---|
| G | R | G | R | G | R | G | R | } Lap1 → TRANSMISSION |
| B | G | B | G | B | G | B | G | |
| G | R | G | R | G | R | G | R | } Lap2 |
| B | G | B | G | B | G | B | G | |
| G | R | G | R | G | R | G | R | } Lap3 → TRANSMISSION |
| B | G | B | G | B | G | B | G | |
| G | R | G | R | G | R | G | R | } Lap4 |
| B | G | B | G | B | G | B | G | |

|   |   |   |   |   |   |   |   |   |
|---|---|---|---|---|---|---|---|---|
| G | R | G | R | G | R | G | R | } Lbp1-1 → TRANSMISSION |
| B | G | B | G | B | G | B | G | |
| G | R | G | R | G | R | G | R | } Lbp1-2 |
| B | G | B | G | B | G | B | G | |
| G | R | G | R | G | R | G | R | } Lbp1-3 → TRANSMISSION |
| B | G | B | G | B | G | B | G | |
| G | R | G | R | G | R | G | R | } Lbp1-4 |
| B | G | B | G | B | G | B | G | |

128B

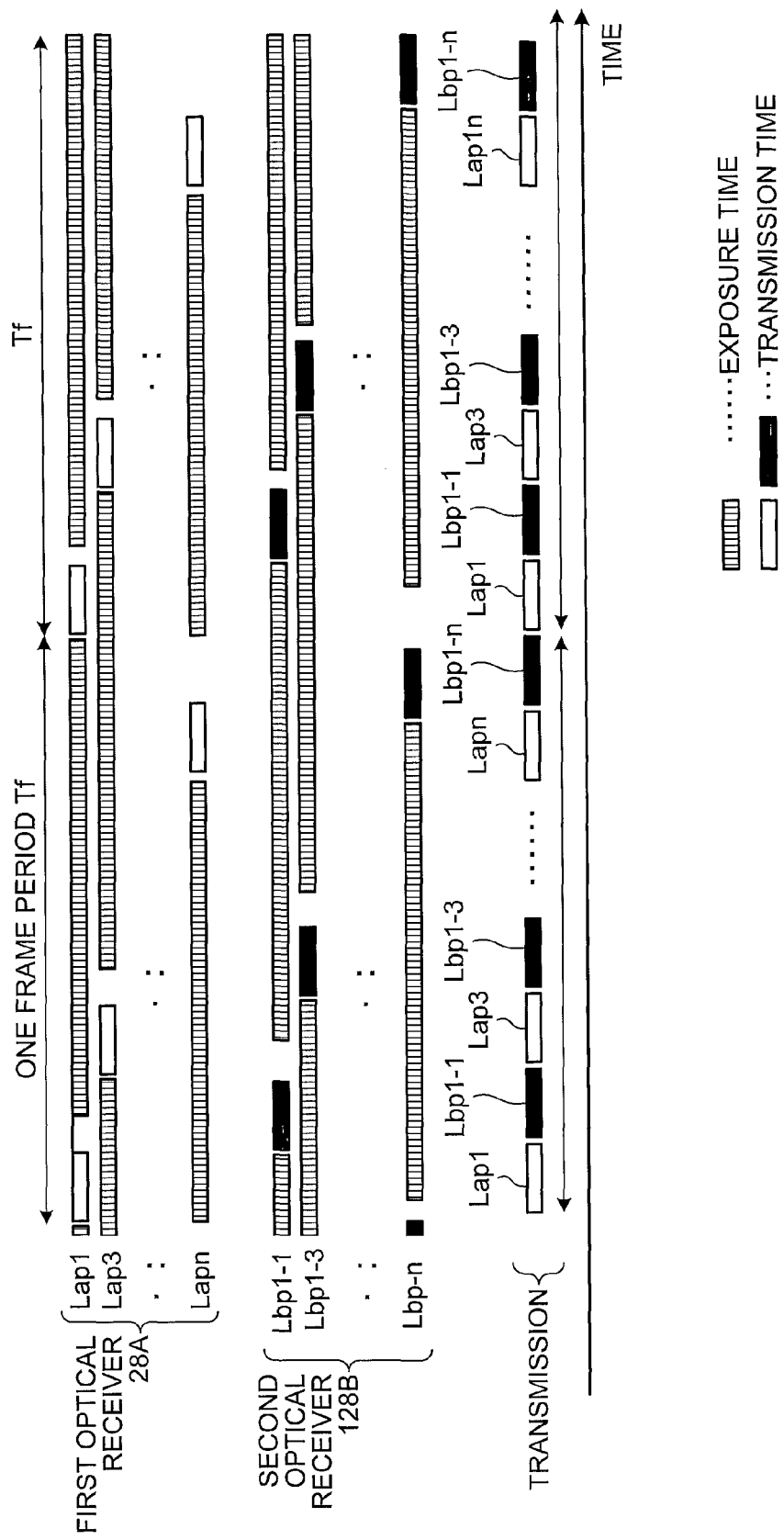

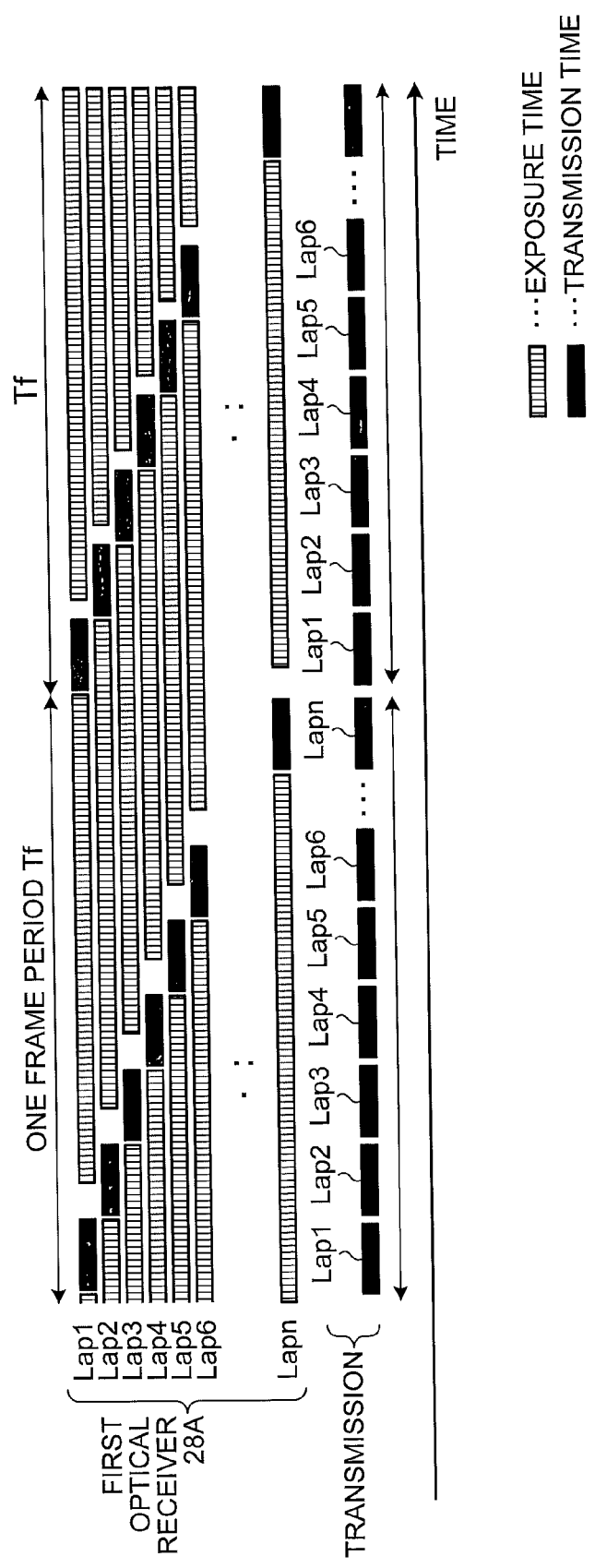

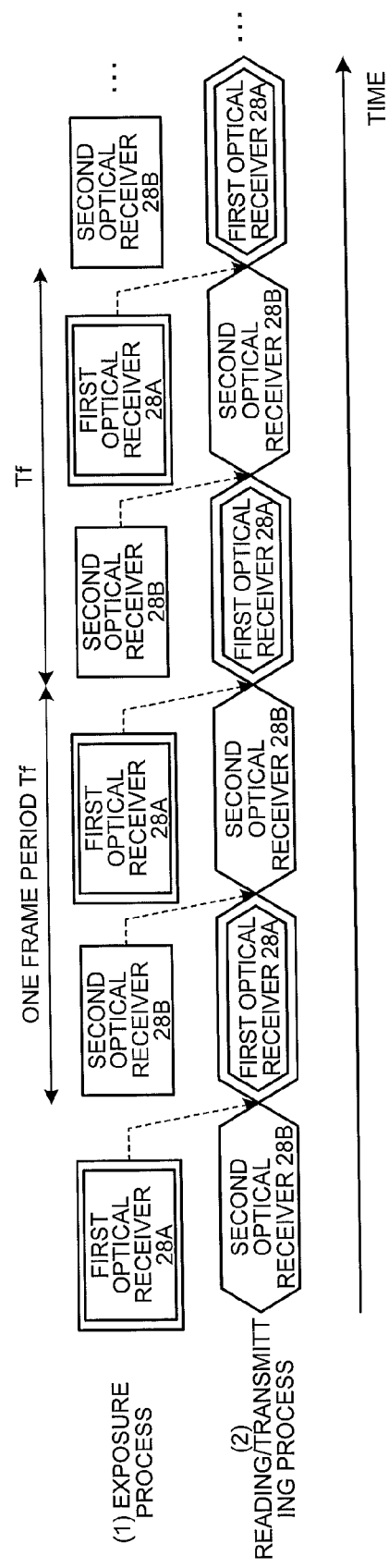

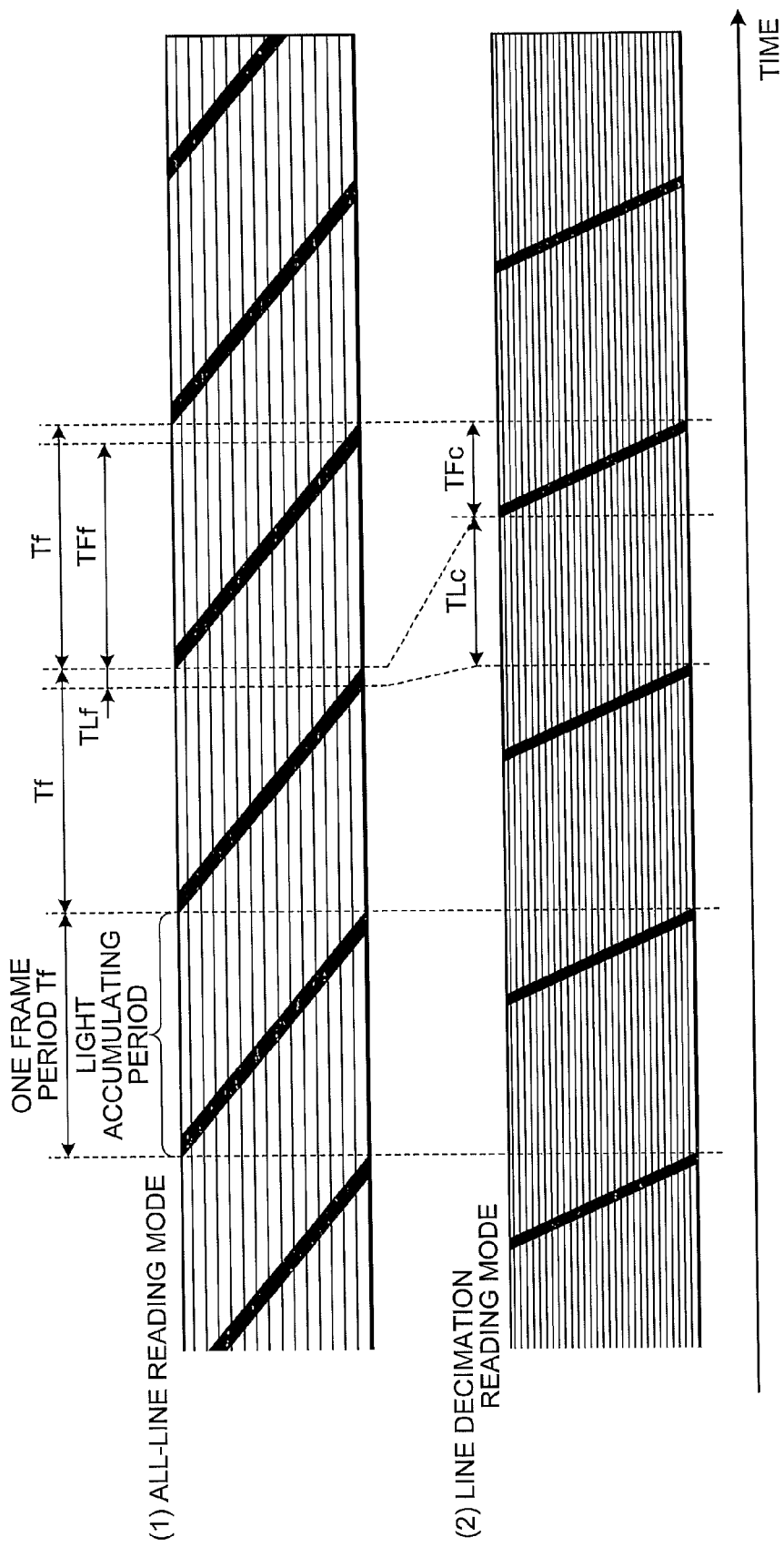

IMAGING APPARATUS

CROSS REFERENCES TO RELATED APPLICATIONS

This application is a continuation of PCT international application Ser. No. PCT/JP2012/070366 filed on Aug. 9, 2012 which designates the United States, incorporated herein by reference, and which claims the benefit of priority from Japanese Patent Applications No. 2011-177692, filed on Aug. 15, 2011, incorporated herein by reference.

BACKGROUND OF THE INVENTION

1. Field of the Invention

The present invention relates to an imaging apparatus including a plurality of imaging units, each of which can output, as pixel information, an electric signal after photoelectric conversion from a pixel arbitrarily designated as a reading target out of a plurality of pixels for imaging.

2. Description of the Related Art

Conventionally, in a medical field, endoscope systems are used when the inside of organs of subjects is observed. Generally, the endoscope system is one type of imaging apparatus capturing an in-vivo image by inserting a flexible insertion portion forming a lengthy thin shape into a body cavity of a subject such as a patient, emitting white light onto a body tissue of the inside of the body cavity through the inserted insertion portion, and receiving reflective light using an imaging unit arranged in the distal end of the insertion portion. An image signal of the body image captured as above is transmitted to an image processing apparatus arranged outside the body through a transmission cable disposed inside the insertion portion, image processing is performed for the body image by the image processing apparatus, and the processed image is displayed on a monitor of the endoscope system. A user such as a doctor observes the inside of the body cavity through the in-vivo image displayed on the monitor.

As an imaging apparatus including an endoscope system, for example, in Japanese Patent Application Laid-open No. 2010-130570, a configuration has been proposed in which two imaging units are arranged, two transmission paths and two image processing units are arranged in correspondence with the imaging units, and images captured by the imaging units can be simultaneously displayed. In addition, as an imaging apparatus including an endoscope system, a configuration has been proposed in which a switching mechanism or an adjustment mechanism of imaging optical systems and filters is arranged, and a color image and another image are acquired using one imaging device.

SUMMARY OF THE INVENTION

An imaging apparatus according to one aspect of the present invention includes: first and second imaging units each being capable of outputting, as pixel information, an electric signal after photoelectric conversion from a pixel arbitrarily set as a reading target among a plurality of pixels for imaging; a reading unit that reads the pixel information from the pixel set as the reading target in each of the first and second imaging units; a control unit that sets the pixel as the reading target in each of the first and second imaging units in a manner such that the pixel information is alternately read from the first and second imaging units by the reading unit, and controls timing of exposure processes in the first and second imaging units and timing of reading processes of the pixel information for the first and second imaging units by the reading unit, to be correlated with one another; a transmission unit that transmits the pixel information read from each of the first and second imaging units in a same transmission path; and an image processing unit that generates an image based on the pixel information transmitted by the transmission unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7C is a diagram for describing the process of transmitting pixel information according to the first embodiment;

FIG. 8C is a diagram for describing the process of transmitting pixel information according to Modified Example 1 of the first embodiment;

FIG. 10A is a diagram for describing reading target pixels of a first optical receiver according to Modified Example 2 of the first embodiment;

FIG. 10B is a diagram for describing reading target pixels of a second optical receiver according to Modified Example 2 of the first embodiment;

FIG. 11 is a diagram for describing a reading process and a pixel signal transmitting process according to Modified Example 2 of the first embodiment;

FIG. 12 is a diagram for describing another example of a reading process and a pixel signal transmitting process according to Modified Example 2 of the first embodiment;

FIG. 13 is a diagram for describing exposure processes in first and second optical receivers according to a second embodiment and processes of reading pixel information for the first and second optical receivers;

FIG. 14 is a diagram for describing a simultaneous exposure time between an all-line reading mode and a line decimation reading mode;

DETAILED DESCRIPTION OF THE PREFERRED EMBODIMENTS

Figure 1:
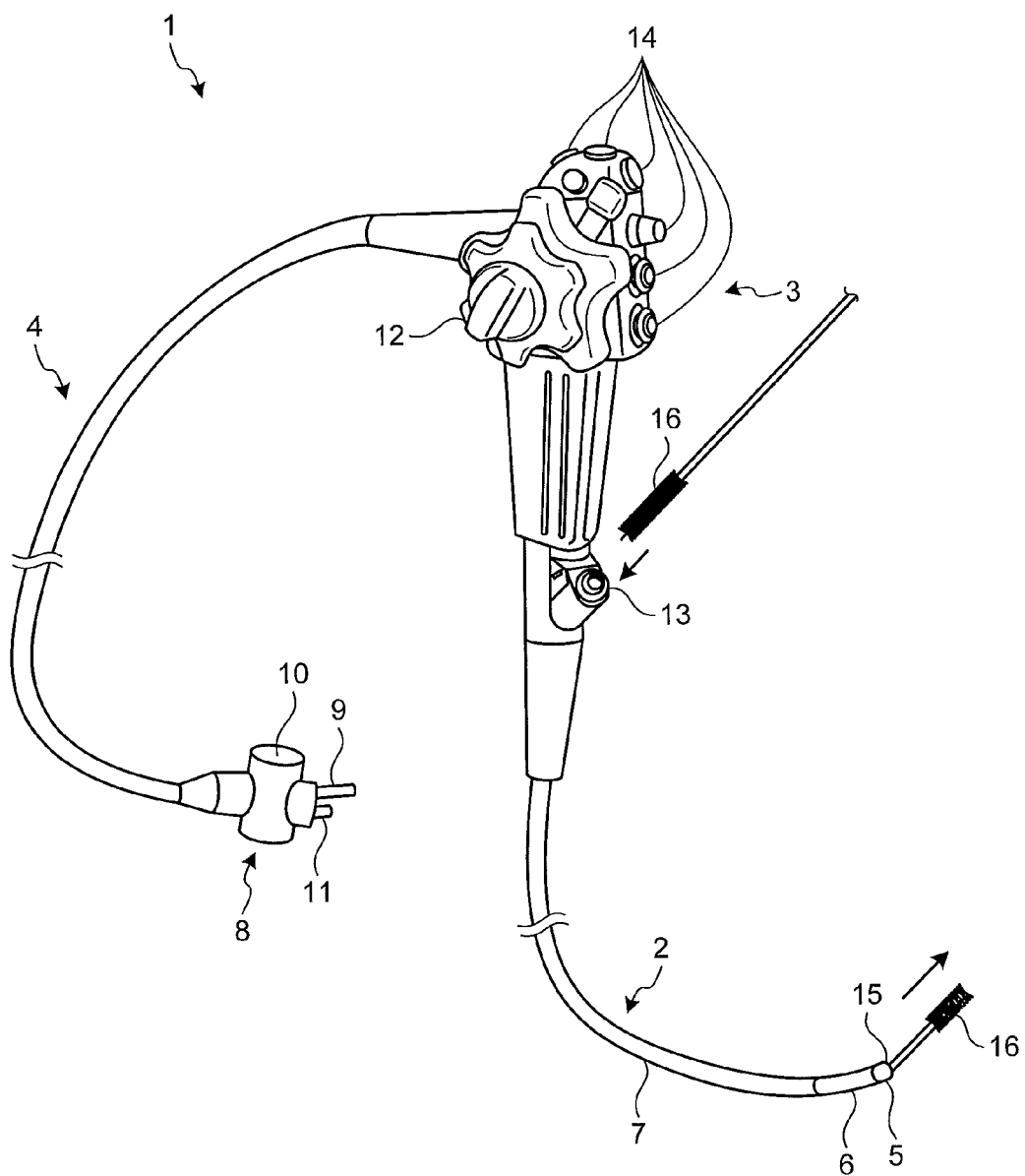
FIG. 1 is a schematic diagram that illustrates the configuration of an endoscope portion according to a first embodiment.

Hereinafter, medical endoscope systems each including imaging devices in the distal end of an insertion portion and capturing and displaying an image of the inside of a body cavity of a subject such as a patient will be described as embodiments of the present invention. However, the present invention is not limited to the embodiments. In the drawings, the same reference numerals are used to indicate the same or similar parts. Here, diagrams are schematically illustrated, and it should be noted that the relation between the thickness and the width of each member, the ratio of each member, and the like are different from those that are actually realized. Between the diagrams, portions having a mutually-different size relation or mutually-different ratios are included.

First Embodiment

First, an endoscope system according to a first embodiment will be described. In the first embodiment, an endoscope system capable of acquiring an ordinary color image according to white light and another image such as fluorescent observation image other than the color image will be described as an example. FIG. 1 is a schematic diagram that illustrates the configuration of an endoscope portion of the endoscope system according to the first embodiment. As illustrated in FIG. 1, an endoscope 1 according to the first embodiment includes a thin and long insertion portion 2, an operating unit 3 that is gripped by an endoscope apparatus operator on the proximal end side of the insertion portion 2, and a flexible universal code 4 that extends from a side portion of the operating unit 3. The universal code 4 has a light guide cable, an electric system cable, and the like built therein.

The insertion portion 2 includes a distal end portion 5 having a CMOS sensor built therein as an imaging device, a bending portion 6 that is configured by a plurality of bending pieces and can be bent, and an elongated flexible tube portion 7 that is disposed on the proximal end side of the bending portion 6 and has flexibility.

In an end portion of the universal code 4, a connector portion 8 is disposed. In the connector portion 8, a light guide connector 9 that is connected to a light source device in a detachable manner, an electric contact portion 10 that is connected to a control device for transmitting an electric signal of a subject image that is converted in a photoelectrical manner using the CMOS sensor to the control device used for signal processing, an air supply cap 11 used for supplying air to a nozzle disposed in the distal end portion 5, and the like are disposed. Here, the light source device includes a white light source, a specialized light source, or the like and supplies light transmitted from the white light source or the specialized light source to the endoscope 1 connected through the light guide connector 9 as illumination light. The control device is a device that supplies power to the imaging device and receives an electric signal that is converted in a photoelectrical manner from the imaging device, processes an electric signal captured by the imaging device and displays an image on a display unit connected thereto, and performs control of gain adjustment of the imaging device and the like and output of a driving signal used for driving.

In the operating unit 3, a bending knob 12 that bends the bending portion 6 in the vertical direction and the horizontal direction, a treatment tool inserting portion 13 that inserts a treatment tool 16 such as biopsy forceps or a laser probe into the inside of a body cavity, and a plurality of switches 14 that are used for operating the control device or the light source device or a peripheral device such as a means for supplying air, water, gas, or the like are disposed. The treatment tool 16 inserted from the treatment tool inserting portion 13 and is let out from an opening portion 15 formed in the distal end of the insertion portion 2 through a treatment tool channel disposed inside thereof. For example, in a case where treatment tool 16 is biopsy forceps, biopsy for extracting an affected part using the biopsy forceps is performed.

Figure 2:
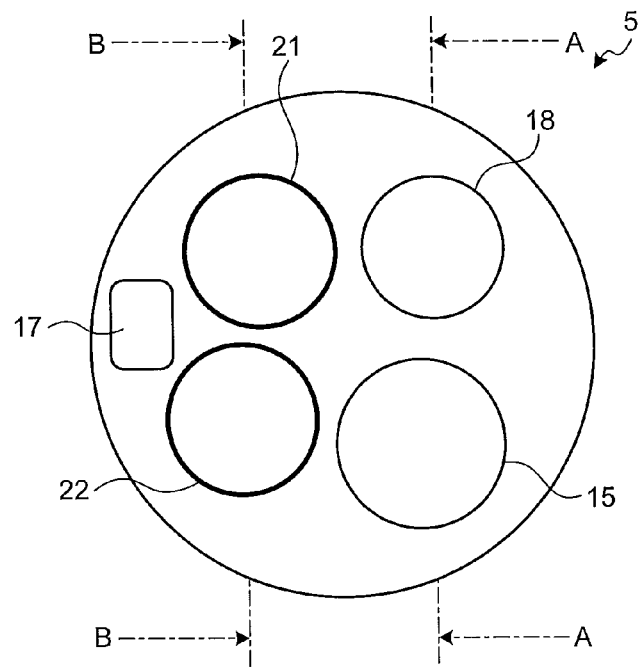
FIG. 2 is a diagram that illustrates a distal end face of a distal end portion of the endoscope illustrated in FIG. 1.
Figure 3:
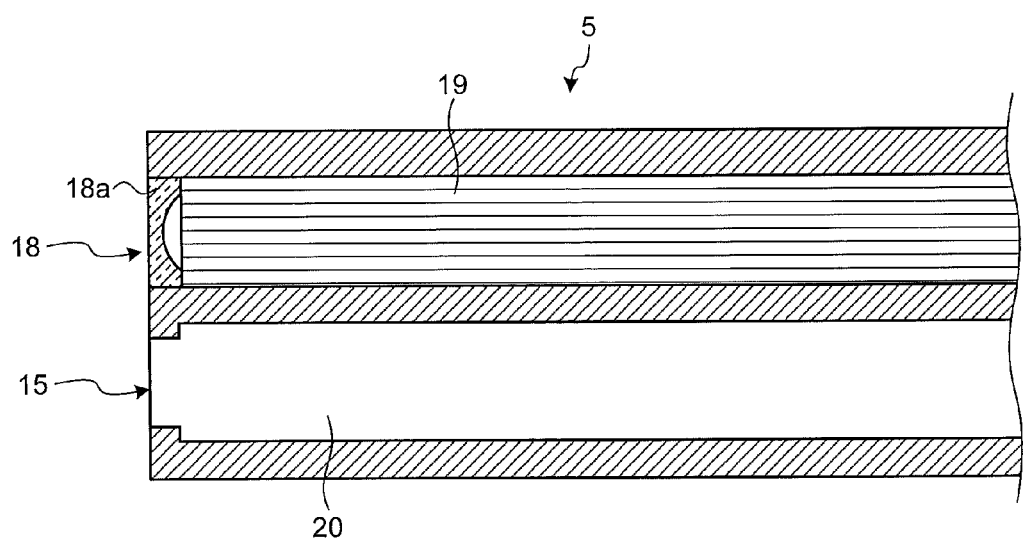
FIG. 3 is a diagram that illustrates a part of a cross-section of the distal end portion, which is illustrated in FIG. 2, taken along line A-A.
Figure 4:
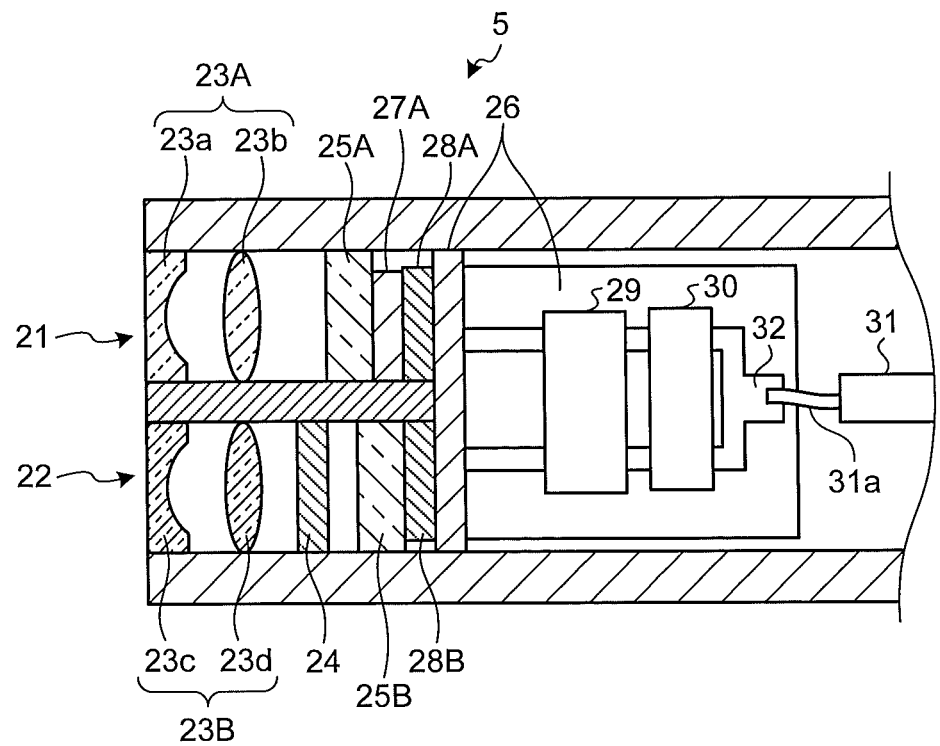
FIG. 4 is a diagram that illustrates a part of a cross-section of the distal end portion, which is illustrated in FIG. 2, taken along line B-B.

Next, the configuration of the distal end portion 5 of the insertion portion 2 will be described. FIG. 2 is a diagram that illustrates a distal end face of the distal end portion 5 of the endoscope 1 illustrated in FIG. 1. FIG. 3 is a diagram that illustrates a part of a cross-section of the distal end portion 5, which is illustrated in FIG. 2, taken along line A-A. FIG. 4 is a diagram that illustrates a part of a cross-section of the distal end portion 5, which is illustrated in FIG. 2, taken along line B-B.

As illustrated in FIG. 2, on the distal end face of the distal end portion 5 of the endoscope 1 illustrated in FIG. 1, the opening portion 15 for letting out the treatment tool, a cleaning nozzle 17, an illumination window 18 through which illumination light is emitted, and observation windows 21 and 22 are disposed.

As illustrated in FIG. 3, in the illumination window 18, white light or specialized light supplied from the light source device through a light guide 19 configured by a bundle of glass fibers or the like is emitted from an illumination lens 18a. The opening portion 15 for letting out the treatment tool communicates with a treatment tool channel 20.

As illustrated in FIG. 4, the observation windows 21 and 22 are closed. Light incident from the outside through the observation window 21 is incident to a first optical system 23A that is configured by a plurality of lenses 23a and 23b, is collected, and then, is incident to a first optical receiver 28A. In addition, light incident from the outside through the observation window 22 is incident to a second optical system 23B that is configured by a plurality of lenses 23c and 23d, is collected, and then, is incident to a second optical receiver 28B.

The first optical receiver 28A includes a plurality of pixels, which are used for capturing images, two-dimensionally arranged in a matrix pattern and is arranged such that light emitted from the first optical system 23A is incident thereto. The first optical receiver 28A captures an image of the inside of a body cavity by receiving light incident through the first optical system 23A. On a light receiving face side of the first optical receiver 28A, a cover glass 25A is disposed. Between the cover glass 25A and the first optical receiver 28A, an on-chip filter 27A is disposed in which filters of red (R), green (G), and blue (B) are disposed in correspondence with the arrangement of pixels of the first optical receiver 28A, and the first optical receiver 28A captures color images. Here, the on-chip filter 27A may be a complementary-color filter in which filters of cyan, magenta, yellow, and green are arranged.

The second optical receiver 28B includes a plurality of pixels, which are used for capturing images, two-dimensionally arranged in a matrix pattern and is arranged such that light emitted from the second optical system 23B is incident thereto. On the light receiving face side of the second optical receiver 28B, a spectral filter 24 that transmits only light of a specified wavelength band and a cover glass 25B are disposed, and the second optical receiver 28B has a characteristic for capturing a fluorescent observation image corresponding to fluorescence of a specified wavelength band as a monochrome image.

Figure 5:
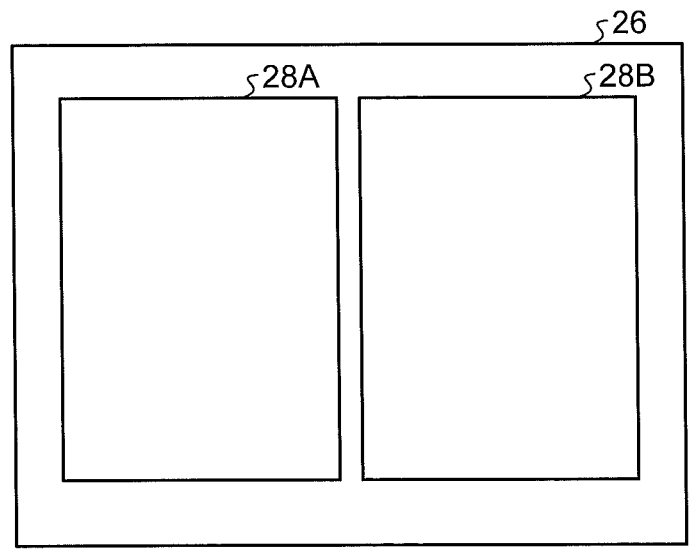
FIG. 5 is a diagram that illustrates a principal face of a basal plate illustrated in FIG. 4.

The first optical receiver 28A and the second optical receiver 28B are mounted on a circuit board 26 together with a driver 29 that instructs image capturing timing to the first and second optical receivers 28A and 28B and supplies power, a conversion circuit 30 that reads image signals acquired by the first and second optical receivers 28A and 28B and converts the image signals into electric signals, and the like. The first and second optical receivers 28A and 28B, as illustrated in FIG. 5, are mounted on the circuit board 26 such that the light receiving faces thereof are horizontally aligned. In the circuit board 26, an electrode 32 is disposed. The electrode 32 is connected to a signal line 31*a* that transmits an electric signal to or from the control device, for example, through an anisotropic conductive resin film. Other than the signal line 31*a* that transmits an image signal that is an electric signal output from each optical receiver, an assembled cable 31 is formed by a plurality of signal lines including a signal line used for transmitting control signal from the control device.

In the endoscope system according to the first embodiment, a CMOS imaging sensor 80 that can read only a pixel of an address that is arbitrarily set out of pixels of the first and second optical receivers 28A and 28B is used as an imaging device. In the endoscope system according to the first embodiment, pixel information is alternately read from the first and second optical receivers 28A and 28B, and the timing of the exposure process performed in the first and second optical receivers 28A and 28B and the timing of a pixel information reading process for the first and second optical receivers 28A and 28B are controlled to be synchronized. Then, in the endoscope system according to the first embodiment, the pixel information read from the first and second optical receivers 28A and 28B is transmitted in the same transmission path, and an image is generated based on the transmitted pixel information.

Figure 6:
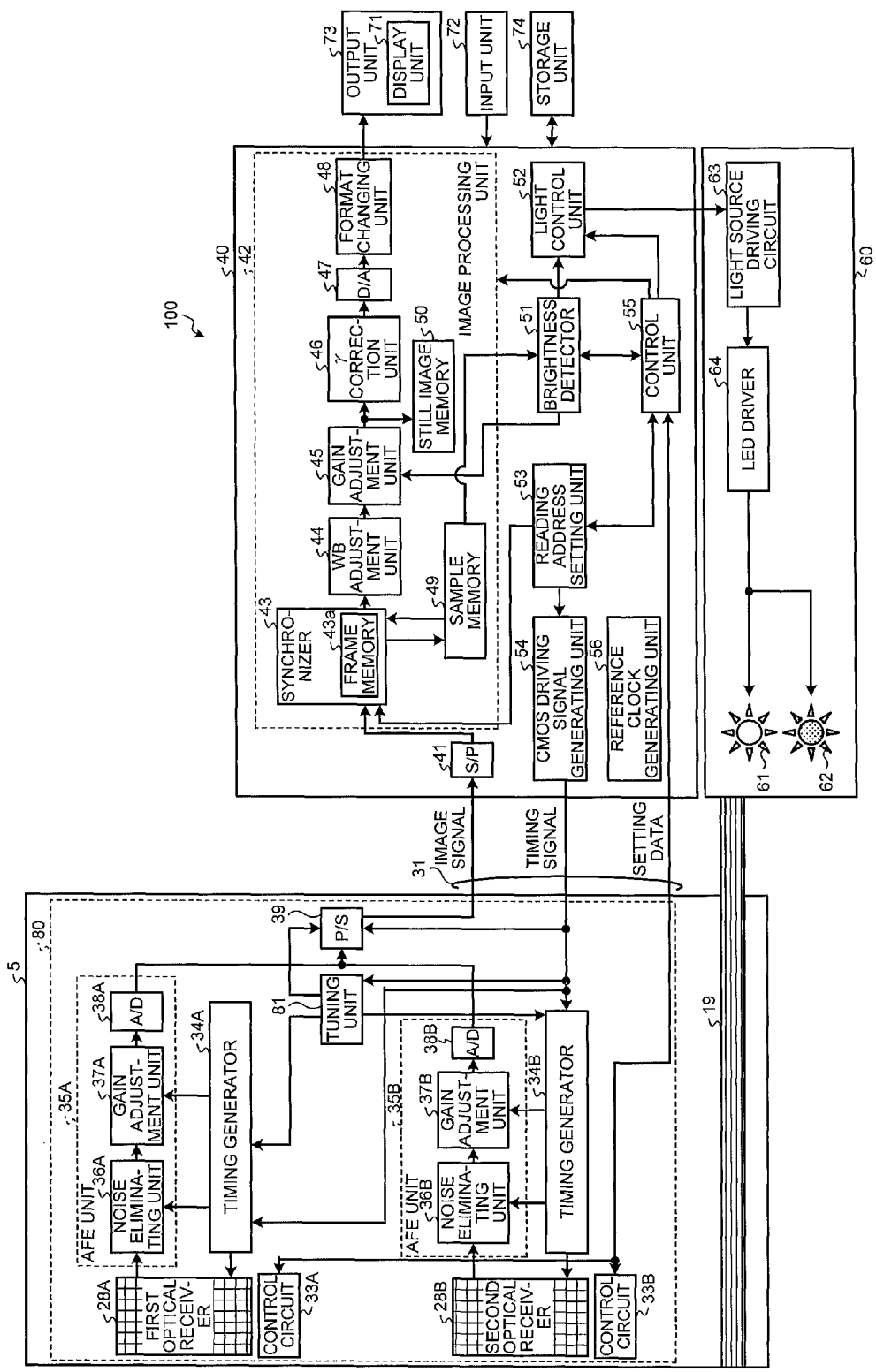
FIG. 6 is a block diagram that illustrates the configuration of an endoscope system according to the first embodiment.

The configuration of the endoscope system according to the first embodiment will be described in detail. FIG. 6 is a block diagram that illustrates the configuration of the endoscope system according to the first embodiment. As illustrated in FIG. 6, the endoscope system 100 according to the first embodiment includes a control device 40 that is connected to the CMOS imaging sensor 80 disposed in the distal end portion 5 through the assembled cable 31 including a plurality of signal lines, a light source device 60 that supplies white light or specialized light, and a display unit 71 that displays an in-vivo image captured by the CMOS imaging sensor 80 and further includes an output unit 73 that outputs information relating to the observation of the inside of a body, and an input unit 72 that inputs various kinds of instruction information necessary for the observation of the inside of a body, and a storage unit 74 that stores an in-vivo image or the like.

In the distal end portion 5, the CMOS imaging sensor 80 is disposed. The CMOS imaging sensor 80 is configured by: an AFE (Analog Front End) unit 35A that is configured by the first optical receiver 28A, a control circuit 33A, a timing generator 34A, a noise eliminating unit 36A, a gain adjustment unit 37A, and an A/D converter 38A; an AFE (Analog Front End) unit 35B that is configured by the second optical receiver 28B, a control circuit 33B, a timing generator 34B, a noise eliminating unit 36B, a gain adjustment unit 37B, and an A/D converter 38B; a P/S converter 39 that converts an input digital signal from a parallel signal into a serial signal; and a tuning unit 81. For example, the first optical receiver 28A, the second optical receiver 28B, and a CMOS sensor peripheral circuit configuring the CMOS imaging sensor 80 are formed as one chip.

Each of the first and second optical receivers 28A and 28B outputs an electric signal after photoelectric conversion from a pixel that is arbitrarily selected as a reading target out of a plurality of pixels, which are two-dimensionally arranged in a matrix pattern, for capturing an image as pixel information. Each pixel information includes a luminance value. The first optical receiver 28A serves as a first imaging unit according to claims. The first optical receiver 28A captures a color image according to white light. The second optical receiver 28B, as described above, serves as a second imaging unit according to the claims and captures a monochrome image that is a fluorescent observation image corresponding to fluorescence of a specified wavelength band.

The control circuit 33A controls an exposure process performed in the first optical receiver 28A, an image capturing process for the first optical receiver 28A, the image capturing speed of the first optical receiver 28A, a process of reading the pixel information from the first optical receiver 28A, and a process of transmitting the read pixel information under the control of the tuning unit 81 to be described later in accordance with setting data output from the control device 40. The control circuit 33B controls an exposure process performed in the second optical receiver 28B, an image capturing process for the second optical receiver 28B, the image capturing speed of the second optical receiver 28B, a process of reading the pixel information from the second optical receiver 28B, and a process of transmitting the read pixel information under the control of the tuning unit 81 to be described later.

The timing generator 34A outputs an electric signal after photoelectric conversion from a pixel of a position (address) designated as a reading target out of a plurality of pixels configuring the first optical receiver 28A as pixel information in accordance with the reading sequence based on the setting in a reading address setting unit 53 under the control of the tuning unit 81 to be described later. The timing generator 34B has the same function as that of the timing generator 34A and outputs an electric signal after photoelectric conversion from a pixel of a position designated as a reading target out of a plurality of pixels configuring the second optical receiver 28B as pixel information.

The noise eliminating unit 36A eliminates a noise of the signal of the pixel information output from a specified pixel of the first optical receiver 28A. The gain adjustment unit 37A amplifies a luminance value of the pixel information output from the noise eliminating unit 36A with an amplification rate instructed by the setting data output from a control unit 55 and then outputs the amplified luminance value to the A/D converter 38A. The A/D converter 38A converts the signal of the pixel information from which the noise has been eliminated from an analog signal into a digital signal and outputs the converted signal to the P/S converter 39. In addition, the noise eliminating unit 36B eliminates a noise of a signal of the pixel information output from a specified pixel of the second optical receiver 28B. The gain adjustment unit 37B amplifies a luminance value of the pixel information output from the noise eliminating unit 36B with an amplification rate instructed by the setting data output from the control unit 55 and then outputs the amplified luminance value to the A/D converter 38B. The A/D converter 38B converts the signal of the pixel information from which the noise has been eliminated from an analog signal into a digital signal and outputs the converted signal to the P/S converter 39.

The P/S converter 39 converts the pixel information read from the first optical receiver 28A by the timing generator 34A and the AFE unit 35A and the pixel information read from the second optical receiver 28B by the timing generator 34B and the AFE unit 35B into image signals as serial signals and then, outputs the converted image signals to specified signal lines of the assembled cable 31. The timing generator 34A, the AFE unit 35A, the timing generator 34B, and the AFE unit 35B serve as a reading unit according to the claims.

The tuning unit 81 sets pixels as a reading target of the first and second optical receivers 28A and 28B in accordance with the setting in the reading address setting unit 53 in a manner such that pixel information is read alternately from the first and second optical receivers 28A and 28B by the timing generators 34A and 34B and the AFE units 35A and 35B. The tuning unit 81 controls the timing of the exposure processes in the first and second optical receivers 28A and 28B and the timing of the processes of reading the pixel information for the first and second optical receivers 28A and 28B, which are performed by the timing generators 34A and 34B and the AFE units 35A and 35B, to be correlated with each other. Then, the pixel information read from the first and second optical receivers 28A and 28B is transmitted through the same transmission path. In other words, the pixel information read from the first and second optical receivers 28A and 28B through a specified signal line of the assembled cable 31 is output to the control device 40 through the same signal line out of signal lines in the assembled cable 31.

The control device 40 causes an in-vivo image to be displayed on the display unit 71 by processing an image signal and controls each element of the endoscope system 100. The control device 40 includes an S/P converter 41, an image processing unit 42, a brightness detector 51, a light control unit 52, the reading address setting unit 53, a CMOS driving signal generating unit 54, the control unit 55, and a reference clock generating unit 56.

The S/P converter 41 converts an image signal that is a digital signal received from the distal end portion 5 from a serial signal into a parallel signal.

The image processing unit 42 generates an image displayed on the display unit 71 based on an image signal in a parallel form output from the S/P converter 41, in other words, the pixel information of pixels alternately read from the first and second optical receivers 28A and 28B by the timing generators 34A and 34B and the AFE units 35A and 35B. The image processing unit 42 generates an in-vivo image based on the address of the pixel of the first optical receiver 28A and the address of the pixel of the second optical receiver 28B that are read by the timing generators 34A and 34B and the AFE units 35A and 35B. The image processing unit 42 adjusts image processing timing in correspondence with output timing of the image signal in the parallel form output from the S/P converter 41.

The image processing unit 42 includes a synchronizer 43, a WB adjustment unit 44, a gain adjustment unit 45, a γ correction unit 46, a D/A converter 47, a format changing unit 48, a sample memory 49, and a still image memory 50.

The synchronizer 43 inputs input image signals of R, G, and B pixels to memories (not illustrated in the figure) arranged for each pixel, sequentially updates and maintains the value of each memory with each input image signal in correspondence with the addresses of the pixels of the first and second optical receivers 28A and 28B, which are read by the timing generators 34A and 34B and the AFE units 35A and 35B, and synchronizes the image signals of the three memories as RGB image signals. The synchronizer 43 maps each pixel information output from the S/P converter 41 with one of the first and second optical receivers 28A and 28B from which the pixel information is read and temporarily stores the information in a frame memory 43a. The synchronized RGB image signals are sequentially output to the WB adjustment unit 44, and some of the synchronized RGB image signals are output also to the sample memory 49 for an image analysis such as the detection of brightness and are stored.

The WB adjustment unit 44 adjusts white balance of the RGB image signals. The gain adjustment unit 45 adjusts the gains of the RGB image signals. The γ correction unit 46 converts the gray scales of the RGB image signals in accordance with the display unit 71.

The D/A converter 47 converts the RGB image signals after the gray scale conversion from digital signals to analog signals. The format changing unit 48 changes the format of the image signals converted into the analog signals to a format such as high definition television and outputs the converted signals to the display unit 71. As a result, one in-vivo image is displayed on the display unit 71. In addition, some of the RGB signals of which the gains are adjusted by the gain adjustment unit 45 is also stored in the still image memory 50 for displaying a still image, displaying an enlarged image, or displaying a highlighted image.

The brightness detector 51 detects a brightness level corresponding to each pixel based on the RGB image signals stored in the sample memory 49 and stores the detected brightness level in a memory disposed inside the brightness detector 51. In addition, the brightness detector 51 calculates a gain adjustment value and a light emission amount based on the detected brightness levels. The calculated gain adjustment value is output to the gain adjustment unit 45, and the calculated light emission amount is output to the light control unit 52. In addition, a detection result acquired by the brightness detector 51 is output also to the control unit 55.

The light control unit 52, under the control of the control unit 55, sets a current amount supplied to each light source and a drive condition of a darkening filter based on the light emission amount output from the brightness detector 51 and outputs a light source synchronization signal including the set condition to the light source device 60. The light control unit 52 sets the type, the light emission amount, and the light emission timing of light emitted by the light source device 60.

The reading address setting unit 53 can arbitrarily set reading target pixels and the reading sequence in the optical receivers 28A and 28B. In other words, the reading address setting unit 53 can arbitrarily set the addresses of the pixels of the first and second optical receivers 28A and 28B that are read by the timing generators 34A and 34B and the AFE units 35A and 35B. In addition, the reading address setting unit 53 outputs the set addresses of the reading target pixels to the synchronizer 43.

The CMOS driving signal generating unit 54 generates a drive timing signal used for driving the optical receivers 28A and 28B and the CMOS sensor peripheral circuit and outputs the drive timing signal to the timing generators 34A and 34B through a specified signal line included in the assembled cable 31. This timing signal includes the address of the reading target pixel.

The control unit 55 is configured by a CPU and the like and performs drive control of each element, input/output control of information for each element, and information processing for outputting and inputting various kinds of information between elements by reading various programs stored in a memory not illustrated in the figure and performing each processing sequence represented in the programs. The control device 40 outputs setting data used for controlling the capturing of an image to the control circuits 33A and 33B disposed in the distal end portion 5 through a specified signal line included in the assembled cable 31. The setting data includes instruction information used for instructing the exposure processes performed in the first and second optical receivers 28A and 28B, the image capturing speeds of the first and second optical receivers 28A and 28B, and the speeds of reading pixel information from arbitrary pixels of the first and second optical receivers 28A and 28B, instruction information used for instructing the amplification rate of the luminance value of the read pixel information, transmission control information of the read pixel information, and the like.

The control unit 55 changes the reading target pixel and the reading sequence that are set by the reading address setting unit 53. Then, the control unit 55 changes the reading target pixel and the reading sequence, which are set by the reading address setting unit 53, in accordance with an acquisition target image. The control unit 55 controls the process of setting a reading target pixel that is performed by the reading address setting unit 53, the reading process of the timing generators 34A and 34B and the AFE units 35A and 35B, and an image generating process performed by the image processing unit 42 in accordance with the acquisition target image.

The reference clock generating unit 56 generates a reference clock signal that is an operating reference of each element of the endoscope system 100 and supplies the generated reference clock signal to each element of the endoscope system 100.

The light source device 60 performs light emitting process under the control of the control unit 55. The light source device 60 includes a white light source 61, which is configured by an LED or the like, emitting white light, a specialized light source 62 emitting light of one of R, G, and B that is light of a wavelength band other than the wavelength band of the white emission light and is narrow-banded by a narrow-band band pass filter as specialized light, a light source driving circuit 63 that controls the amount of a current supplied to the white light source 61 or the specialized light source 62 or the driving of the darkening filter in accordance with a light source synchronization signal transmitted from the light control unit 52, and an LED driver 64 that supplies a specified amount of current to the white light source 61 or the specialized light source 62 under the control of the light source driving circuit 63. Light emitted from the white light source 61 and the specialized light source 62 is supplied to the insertion portion 2 through the light guide 19 and is output to the outside from the distal end of the distal end portion 5.

In the first embodiment, the pixel information read from two optical receivers including the first and second optical receivers 28A and 28B are transmitted in the same transmission path. Here, one frame period is assumed to be a period that is required for the exposure process performed in the first optical receiver 28A and a reading and transmission process for all the pixels of the first optical receiver 28A. In the first embodiment, by decimating and reading pixel information not from all the pixels of the first optical receiver 28A and all the pixels of the second optical receiver 28B but only from pixels of the first and second optical receivers 28A and 28B, even in a case where pixel information is read from two optical receivers including the first and second optical receivers 28A and 28B, the amount of transmission per unit time of a signal line, which is used for transmitting an image signal, included in the assembled cable 31 is equal to that of a case where pixel information of all the pixels is read from one optical receiver and is transmitted, and the frame period is equal to that of a case where one optical receiver is included. Accordingly, in the first embodiment, images captured by the first and second optical receivers 28A and 28B are simultaneously displayed with the same frame rate as that of a case where one optical receiver is included.

Figure 7A:
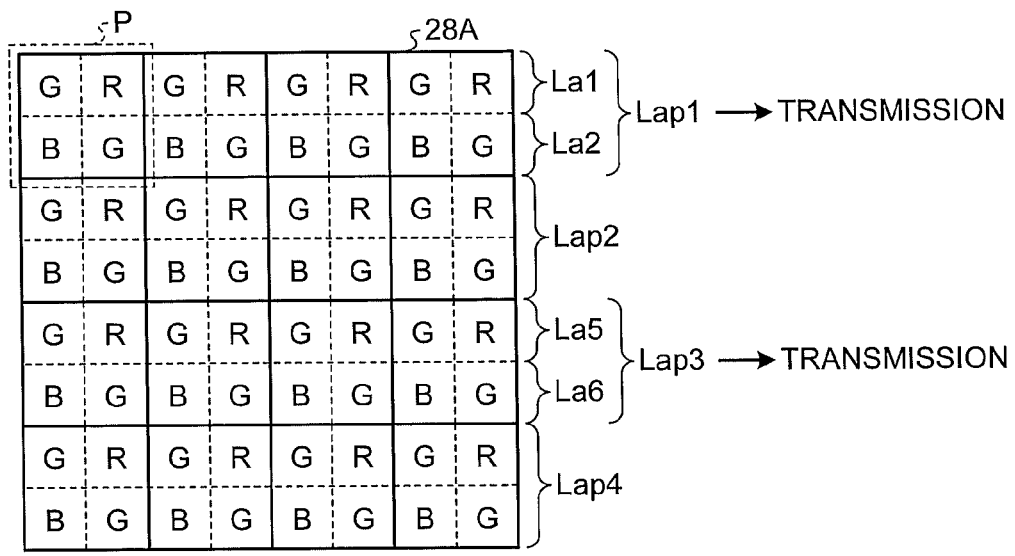
FIG. 7A is a diagram for describing reading target pixels of a first optical receiver according to the first embodiment.
Figure 7B:
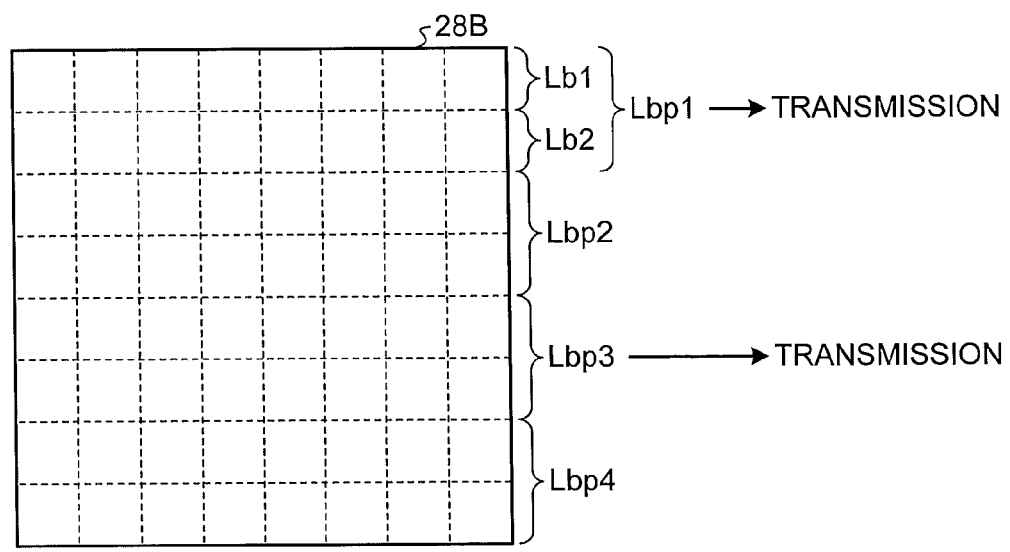
FIG. 7B is a diagram for describing reading target pixels of a second optical receiver according to the first embodiment.

The reading process and the image processing for each optical receiver will be described more specifically with reference to FIGS. 7A to 7D. In a case where a Bayer pattern-type on-chip filter 27A is used, in the first optical receiver 28A, a block P configured by four pixels of R, G, G, and B that are adjacent vertically or horizontally corresponds to one pixel of a display image, as illustrated in FIG. 7A. Accordingly, in order not to separate pixel information corresponding to one pixel of the display image, in the first optical receiver 28A, pixel information is read from every two horizontal lines that are vertically adjacent to each other. Out of horizontal lines configuring the first optical receiver 28A, the pixel information of a line pair Lap1 configured by horizontal lines La1 and La2 and the pixel information of a line pair Lap3 configured by horizontal lines La5 and La6 are read and are transmitted to the control device 40. In contrast to this, the pixel information of a line pair Lap2 next to the line pair Lap1 and the pixel information of a line pair Lap4 next to the line pair Lap3 are neither read nor transmitted. Similarly, as illustrated in FIG. 7B, also in the second optical receiver 28B, pixel information is read from every two horizontal lines that are vertically adjacent to each other. In other words, out of horizontal lines configuring the second optical receiver 28B, the pixel information of a line pair Lbp1 configured by horizontal lines Lb1 and Lb2 and the pixel information of a line pair Lbp3 are read and are transmitted, and the pixel information of a line pair Lbp2 next to the line pair Lbp1 and the pixel information of a line pair Lbp4 next to the line pair Lbp3 are neither read nor transmitted.

At this time, the timings of the exposure process performed in the first and second optical receivers 28A and 28B and the timings of the process of reading pixel information for the first and second optical receivers 28A and 28B are synchronized by the tuning unit 81 such that the pixel information of horizontal lines are alternately read from the first and second optical receivers 28A and 28B at a specified interval of lines and transmitted illustrated as above. More specifically, as illustrated in FIG. 7C, after the pixel information of the horizontal lines La1 and La1 configuring the line pair Lap1 of the first optical receiver 28A is read and transmitted, the pixel information of the horizontal lines Lb1 and Lb2 configuring the line pair Lbp1 of the second optical receiver 28B is read and transmitted, and thereafter, the pixel information of horizontal lines La5 and La6 configuring a line pair Lap3 of the first optical receiver 28A is read and transmitted.

Figure 7D:
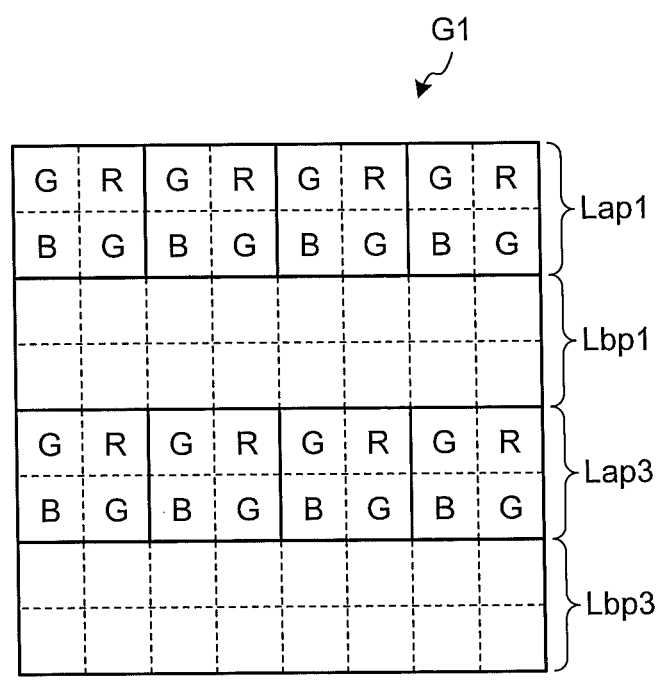
FIG. 7D is a diagram for describing an image generated by an image processing unit according to the first embodiment.

Then, in the control device 40, the image processing unit 42 generates one image by using images captured by the first and second optical receivers 28A and 28B based on the pixel information of line pairs transmitted in order illustrated in FIG. 7C. More specifically, by arranging the pixel information of the line pairs Lap1, Lbp1, Lap3, and Lbp3 transmitted in order as illustrated in FIG. 7C at each vertical one line in the order of transmission as illustrated in FIG. 7D, the image processing unit 42 generates an image G1 in which an ordinary color image and a fluorescent image, which is a specialized image, are overlapped each other. This image G1 is displayed on the display unit 71. Alternatively, the image processing unit 42 separates the pixel information corresponding to the first optical receiver 28A and the pixel information corresponding to the second optical receiver 28B, which are the pixel information of line pairs transmitted in order illustrated in FIG. 7C, from each other, then generates a color image and a fluorescent image, and simultaneously displays the color image and the fluorescent image. The color image and the fluorescent image generated in such a case are images in which the pixel information are decimated every two horizontal lines.

As above, in order to alternately read and alternately transmit pixel information of two imaging units including the first and second optical receivers 28A and 28B, a plurality of pixel information pieces captured by two optical receivers can be appropriately transmitted to the control device 40 by using the same transmission path, and acquisition target images can be appropriately acquired without arranging two image processing units corresponding two optical receivers.

In addition, in the first embodiment, by alternately reading and transmitting the pixel information of horizontal lines while decimating the pixel information of two optical receivers including the first and second optical receivers 28A and 28B at a specified interval of lines, the transmission amount per unit time in a signal line, which transmits an image signal, included in the assembled cable 31 is equivalent to that of a case where pixel information read from all the lines of one optical receiver is transmitted, and the images captured by the first and second optical receivers 28A and 28B can be simultaneously displayed at a frame rate that is the same as that of the configuration in which one optical receiver is included. Therefore, according to the first embodiment, in order to simultaneously display images captured by the first and second optical receivers 28A and 28B, two transmission paths corresponding to two optical receivers do not need to be built on the inside of the insertion portion of the endoscope, and the implementation of the thin and long insertion portion can be maintained.

Furthermore, the tuning unit 81 controls the exposure processes and the reading processes of the first and second optical receivers 28A and 28B so as to be synchronized based on the setting data and the timing signal output from the control device 40. Alternatively, the tuning unit 81 performs control of the exposure process and the reading process of the second optical receiver 28B so as to be synchronized with control of the exposure process and the reading process of the first optical receiver 28A performs by the control circuit 33A based on the setting data and the timing signal output from the control device 40.

In addition, instead of configuring the second optical receiver 28B using a device having the same number of pixels and the same sensitivity level as those of the first optical receiver 28A, the second optical receiver 28B may be configured by a device having pixels less than that of the first optical receiver 28A and a sensitivity level higher than that of the first optical receiver 28A.

Modified Example 1 of the First Embodiment

Next, as Modified Example 1 of the first embodiment, a case will be described in which a second optical receiver 28B performs a so-called binning process.

Figure 8A:
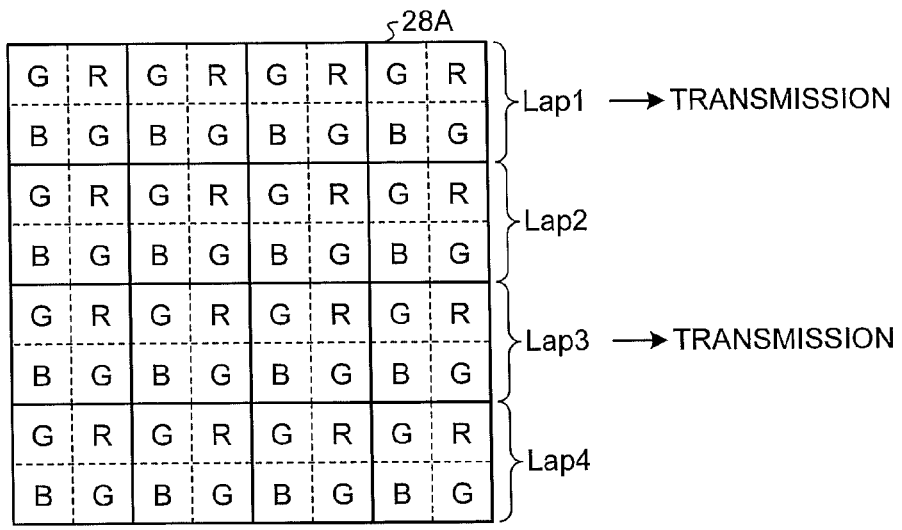
FIG. 8A is a diagram for describing reading target pixels of a first optical receiver according to Modified Example 1 of the first embodiment.

As illustrated in FIG. 8A, similarly to the first embodiment, in a first optical receiver 28A, pixel information is read from every two horizontal lines that are vertically adjacent to each other. In other words, out of horizontal lines configuring the first optical receiver 28A, the pixel information of a line pair Lap1 and the pixel information of a line pair Lap3 are read and transmitted, and the pixel information of a line pair Lap2 and the pixel information of a line pair Lap4 are not read.

Figure 8B:
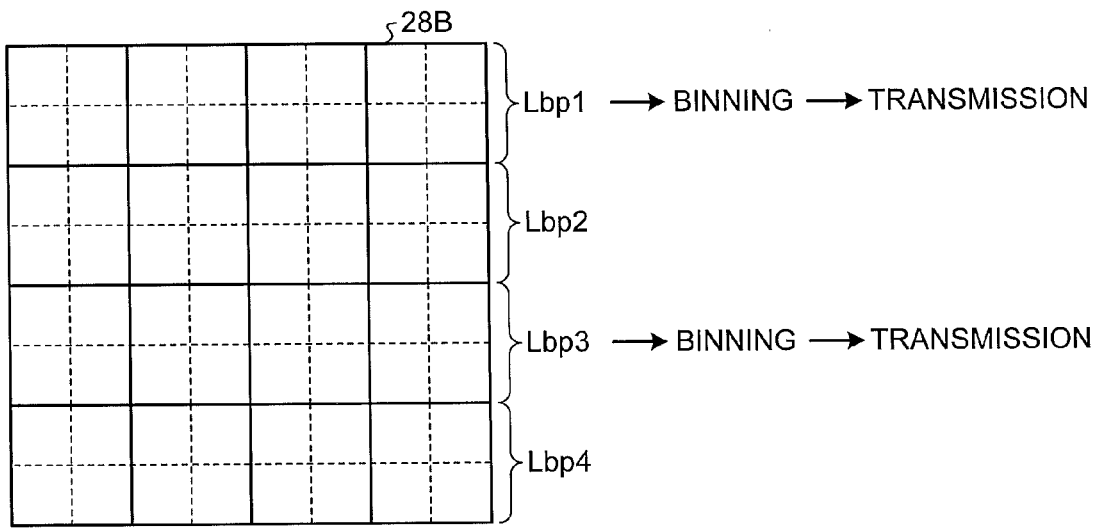
FIG. 8B is a diagram for describing reading target pixels of a second optical receiver according to Modified Example 1 of the first embodiment.

In addition, in the second optical receiver 28B, pixel information is read from horizontal lines at a vertical interval of two horizontal lines. Then, in the second optical receiver 28B, a binning process in which luminance values of pixels are added within a block P in which four pixels are included and are output is performed, and the luminance value is transmitted in units of blocks P. In other words, as illustrated in FIG. 8B, in the second optical receiver 28B, the pixel information of a line pair Lbp1 and the pixel information of a line pair Lbp3 are read, are binning-processed, and are transmitted. In contrast to this, in the second optical receiver 28B, the pixel information of a line pair Lbp2 and the pixel information of a line pair Lbp4 are not read.

Then, as illustrated in FIG. 8C, after the pixel information of horizontal lines La1 and La1 configuring a line pair Lap1 of the first optical receiver 28A is transmitted, the pixel information (Lbp1-B) of horizontal lines Lb1 and Lb2 configuring a line pair Lbp1 of the second optical receiver 28B is transmitted. In such a case, in the second optical receiver 28B, the binning process is performed for each block configured by four pixels, and the information amount of the pixel information (Lbp1-B) of the line pair of the second optical receiver 28B is a quarter of that of the pixel information of the line pair Lap1 of the first optical receiver 28A. Accordingly, the transmission time of the pixel information near the line pair of the second optical receiver 28B is shorter than that of the pixel information near the line pair of the first optical receiver 28A. The tuning unit 81, for the second optical receiver 28B performs control so as to extend an exposure time by allocating a remaining time T1 that remains due to the shortening of the transmission time to the exposure time. Since the intensity of the fluorescent is originally weak, by extending the exposure time, the amount of received fluorescence in the second optical receiver 28B can be increased, whereby the amount of received fluorescence can be detected with high sensitivity.

Figure 8D:
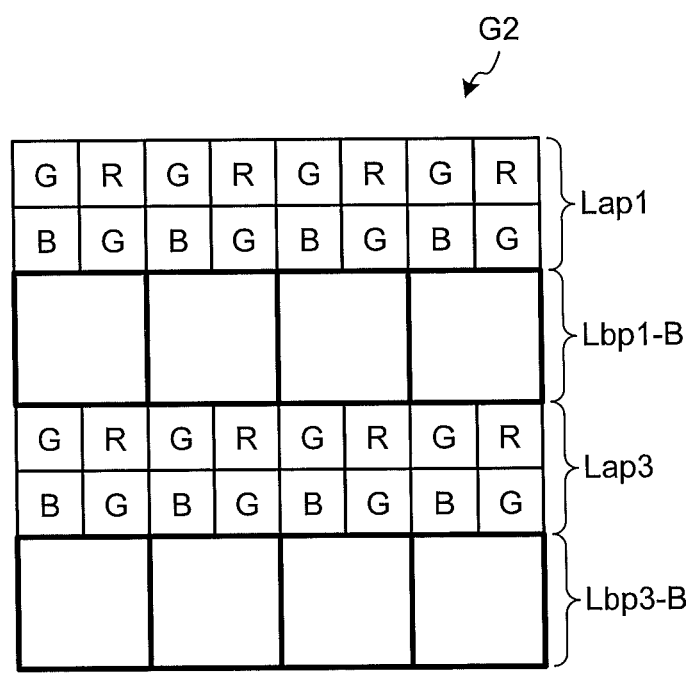
FIG. 8D is a diagram for describing an image generated by an image processing unit according to Modified Example 1 of the first embodiment.

Subsequently, in the control device 40, as the image processing unit 42 vertically arranges the pixel information of line pairs Lap1, Lbp1-B, Lap3, and Lbp3-B at each line in the order of transmission, as illustrated in FIG. 8D, an image G2 is generated in which an ordinary color image according to white light and a fluorescent image that is a specialized image overlap each other. Among these, the pixel information of the line pairs Lbp1 and Lbp3 become pixel information Lbp1-B and Lbp3-B acquired by adding luminance values for each block configured by four pixels. Alternatively, after separating the transmitted pixel information of each line pair into pixel information corresponding to the first optical receiver 28A and pixel information corresponding to the second optical receiver 28B, the image processing unit 42 may generate a color image and a fluorescent image.

As above, in Modified Example 1 of the first embodiment, by causing the second optical receiver 28B to perform a binning process, the amount of transmission per unit time in the signal lines through which the image signals of the assembled cable 31 are transmitted can be smaller than that of the first embodiment. In addition, in Modified Example 1 of the first embodiment, since the transmission time of the pixel information of the second optical receiver 28B can be shortened, the exposure time is extended as that much, whereby image capturing with high sensitivity can be realized in the second optical receiver 28B.

Modified Example 2 of the First Embodiment

Next, as Modified Example 2 of the first embodiment, a case will be described in which an on-chip filter is arranged also in a second optical receiver, and right and left images of colors are simultaneously projected in a first optical receiver and the second optical receiver so as to generate a so-called stereoscopic image.

Figure 9:
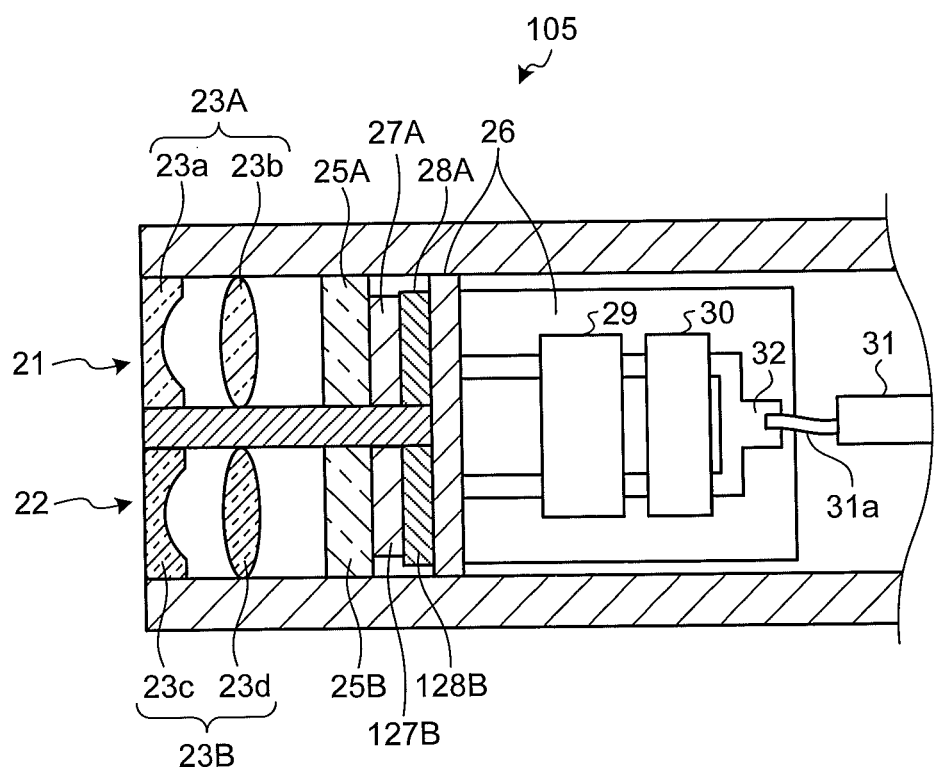
FIG. 9 is a diagram that illustrates a part of a cross-section of a distal end portion of an endoscope according to Modified Example 2 of the first embodiment.

FIG. 9 is a diagram that illustrates a part of a cross-section of a distal end portion of an endoscope according to Modified Example 2 of the first embodiment. As illustrated in FIG. 9, in a distal end portion 105 according to Modified Example 2 of the first embodiment, instead of the second optical receiver 28B, similarly to the first optical receiver 28A, a second optical receiver 128B having characteristics for capturing a color image is arranged, and, on the light receiving face side of the second optical receiver 128B, similarly to the first optical receiver 28A, an on-chip filter 127B having the same configuration as that of the on-chip filter 27A is disposed between the cover glass 25B and the second optical receiver. The first and second optical receivers 28A and 128B have light receiving faces mounted on the circuit board 26 so as to be horizontally aligned, and the first optical receiver 28A, for example, captures a right image, and the second optical receiver 128B, for example, captures a left image.

Also in such a case, similarly to the first embodiment, in the first optical receiver 28A, pixel information is read from every two horizontal lines that are vertically adjacent to each other. In other words, as illustrated in FIGS. 10A and 11, out of horizontal lines configuring the first optical receiver 28A, the pixel information of a line pair Lap1 and the pixel information of a line pair Lap3 are read and transmitted, and the pixel information of a line pair Lap2 and the pixel information of a line pair Lap4 are not read.

Then, also in the second optical receiver 128B, pixel information is read from horizontal lines at an interval of two horizontal lines that are vertically arranged. In other words, as illustrated in FIGS. 10B and 11, in the second optical receiver 128B, the pixel information of a line pair Lbp1-1 and the pixel information of a line pair Lbp1-3 are read and, then are transmitted, and the pixel information of a line pair Lbp1-2 and the pixel information of a line pair Lbp1-4 are not read.

Then, as illustrated in FIG. 11, after the pixel information of the line pair Lap1 of the first optical receiver 28A is transmitted, the pixel information of the line pair Lbp1-1 of the second optical receiver 128B is transmitted, and, thereafter, the pixel information of the line pair Lap3 of the first optical receiver 28A is transmitted. As above, the pixel information of the line pair of the first optical receiver 28A and the pixel information of the line pair of the second optical receiver 128B are alternately transmitted. Then, in the control device, the image processing unit separates the pixel information of the first optical receiver 28A and the pixel information of the line pair of the second optical receiver 128B that are sequentially transmitted within one frame period Tf in an alternating manner for each optical receiver, a right image captured by the first optical receiver 28A and a left image captured by the second optical receiver 128B are generated, and then, the right image and the left image that have been generated are composed to generate one stereoscopic image.

As above, also in Modified Example 2 of the first embodiment in which a right image and a left image are simultaneously acquired, and a stereoscopic image is generated, the pixel information of two optical receivers including the first optical receiver 28A and the second optical receiver 128B is decimated at a specified interval of lines and is alternately read and transmitted, and accordingly, the same advantages as those of the first embodiment are acquired.

In addition, in Modified Example 2 of the first embodiment, in a case where an ordinary two-dimensional image is acquired, the image capturing process may be performed only for the first optical receiver 28A out of the first and second optical receivers 28A and 128B. In such a case, since the image capturing process is performed only for a single optical receiver, as illustrated in FIG. 12, within one frame period Tf, all the line pairs La1 to Lpn of the first optical receiver 28A can be read and transmitted, a decimating and reading process may not be performed. In addition, instead of configuring the second optical receiver 128B to be configured by the same number of pixels as that of the first optical receiver 28A, the number of pixels of the second optical receiver 128B may be smaller than that of the first optical receiver 28A.

Second Embodiment

Next, a second embodiment will be described. An endoscope according to the second embodiment has the same configuration as that of the endoscope according to the first embodiment. FIG. 13 is a diagram for describing exposure processes in first and second optical receivers according to the second embodiment and processes of reading pixel information for the first and second optical receivers.

In the second embodiment, a global shutter mode is employed so as to simultaneously expose all the lines of the optical receiver for a specified period, the tuning unit 81, as illustrated in FIG. 13, divides one frame period Tf into two same periods, the exposure processes in the first and second optical receivers 28A and 28B and the pixel information reading/transmitting processes for the first and second optical receivers 28A and 28B are alternately performed in the divided periods. In a first half period acquired by dividing one frame period Tf into two, the tuning unit 81 allows the first optical receiver 28A to perform a reading/transmitting process and allows the second optical receiver 28B to perform an exposure process. Then, in a second half period acquired by dividing one frame period Tf into two, the tuning unit 81 allows the first optical receiver 28A to perform an exposure process and allows the second optical receiver 28B to perform a reading/transmitting process.

In such a case, the tuning unit 81 controls the reading/transmitting process also for one of the first and second optical receivers 28A and 28B so as to read a pixel signal from a horizontal line at an interval of two lines. As a result, in the second embodiment, the transmission amount per unit time in a signal line, which transmits an image signal, included in the assembled cable 31 is equivalent to that of a case where pixel information read from all the lines of one optical receiver is transmitted, and the images can be simultaneously displayed at a frame rate that is the same as that of the configuration in which one optical receiver is included.

By alternately arranging the pixel information of each line pair of the first optical receiver 28A and the pixel information of each line pair of the second optical receiver 28B for each line pair, the image processing unit 42 generates an image in which an ordinary color image according to white light and a fluorescent image, which is a specialized image, are overlapped each other. Alternatively, the image processing unit 42 generates a color image and a fluorescent image as separate images based on the pixel information of the first optical receiver 28A and the pixel information of the second optical receiver 28B that have been transmitted.

Here, as illustrated in FIG. 14, compared to an all-line reading mode in which pixel information is read from all the lines, in the line decimation reading method in which pixel information is read by decimating lines, the amount of pixel information that is transmitted is small, and accordingly, the reading/transmitting period TFc can be shorter than the reading/transmitting period TFf of the all-line reading mode. In the line decimation reading mode, the simultaneous exposure time TLc for all the lines can be longer than the simultaneous exposure time TLf for all the lines in the all-line reading mode by a length corresponding to a decrease in the reading/transmitting period.

As above, in the second embodiment, by dividing one frame period into two and alternately performing the exposure processes in the first and second optical receivers 28A and 28B and the pixel information reading/transmitting processes for the first and second optical receivers 28A and 28B for each divided period, a plurality of pixel information pieces captured by two optical receivers can be appropriately transmitted to the control device 40 by using the same transmission path, and acquisition target images can be appropriately acquired without arranging two image processing units corresponding two optical receivers.

In addition, in the second embodiment, by reading and transmitting the pixel information of two optical receivers including the first and second optical receivers 28A and 28B while decimating the pixel information at a specified interval of lines, the transmission amount per unit time in a signal line, which transmits an image signal, included in the assembled cable 31 is equivalent to that of a case where pixel information read from all the lines of one optical receiver is transmitted. As a result, in the second embodiment, similarly to the first embodiment, in order to simultaneously display images captured by the first and second optical receivers 28A and 28B, two transmission paths corresponding to two optical receivers do not need to be built on the inside of the insertion portion of the endoscope, and the implementation of the thin and long insertion portion can be maintained.

Furthermore, in the second embodiment, by reading and transmitting the pixel information of two optical receivers including the first and second optical receivers 28A and 28B while decimating the pixel information at a specified interval of lines, the simultaneous exposure time for all the lines can be sufficiently acquired.

Figure 15:
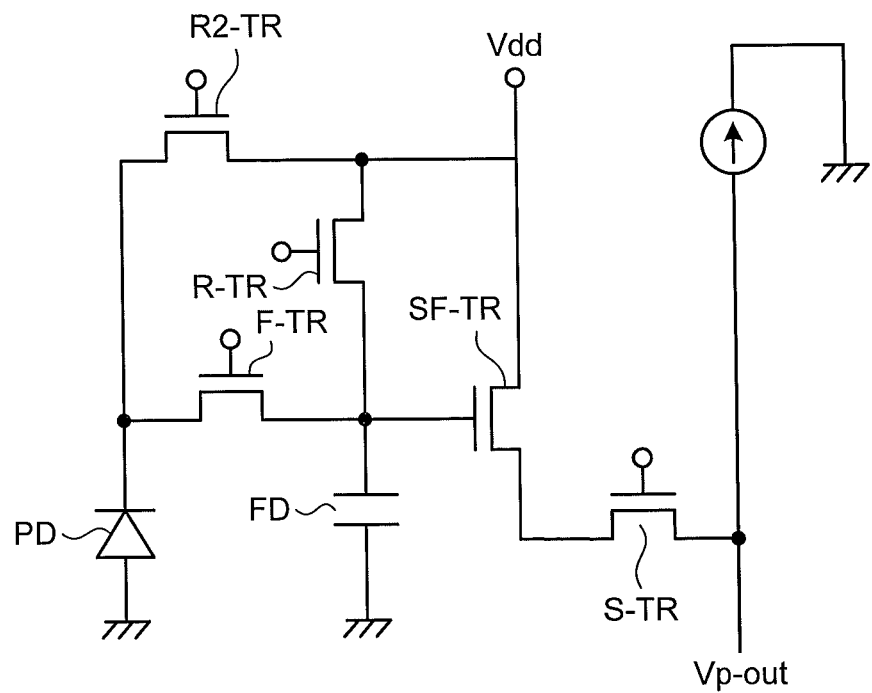
FIG. 15 is a circuit diagram that illustrates the configuration of a unit pixel of an optical receiver.

In addition, the exposure time can be adjusted in units of pixels in the first and second optical receivers 28A and 28B. FIG. 15 is a circuit diagram that illustrates the configuration of a unit pixel of an optical receiver. As illustrated in FIG. 15, the unit pixel includes: a photo diode PD that performs photoelectric conversion of incident light to a signal charge amount corresponding to the light amount thereof and accumulates electric charges; a transmission transistor F-TR that transmits signal charge converted and accumulated in the photodiode PD in the On period to a capacitor FD; a first reset transistor R-TR that discharges the signal charge accumulated in the capacitor FD in the On period so as to be reset; a second reset transistor R2-TR that discharges signal charge accumulated in the photodiode PD in the On period such that the photodiode PD is reset; and an output transistor SF-TR that converts a voltage (converted signal voltage) read by the transmission transistor F-TR at the time of turning on a selection transistor S-TR into a pixel signal Vp-out of the same level and outputs the converted pixel signal to a specified signal line. The selection transistor S-TR is controlled to be turned on in a case where the horizontal line including the unit pixel is selected as a reading target line.

Figure 16:
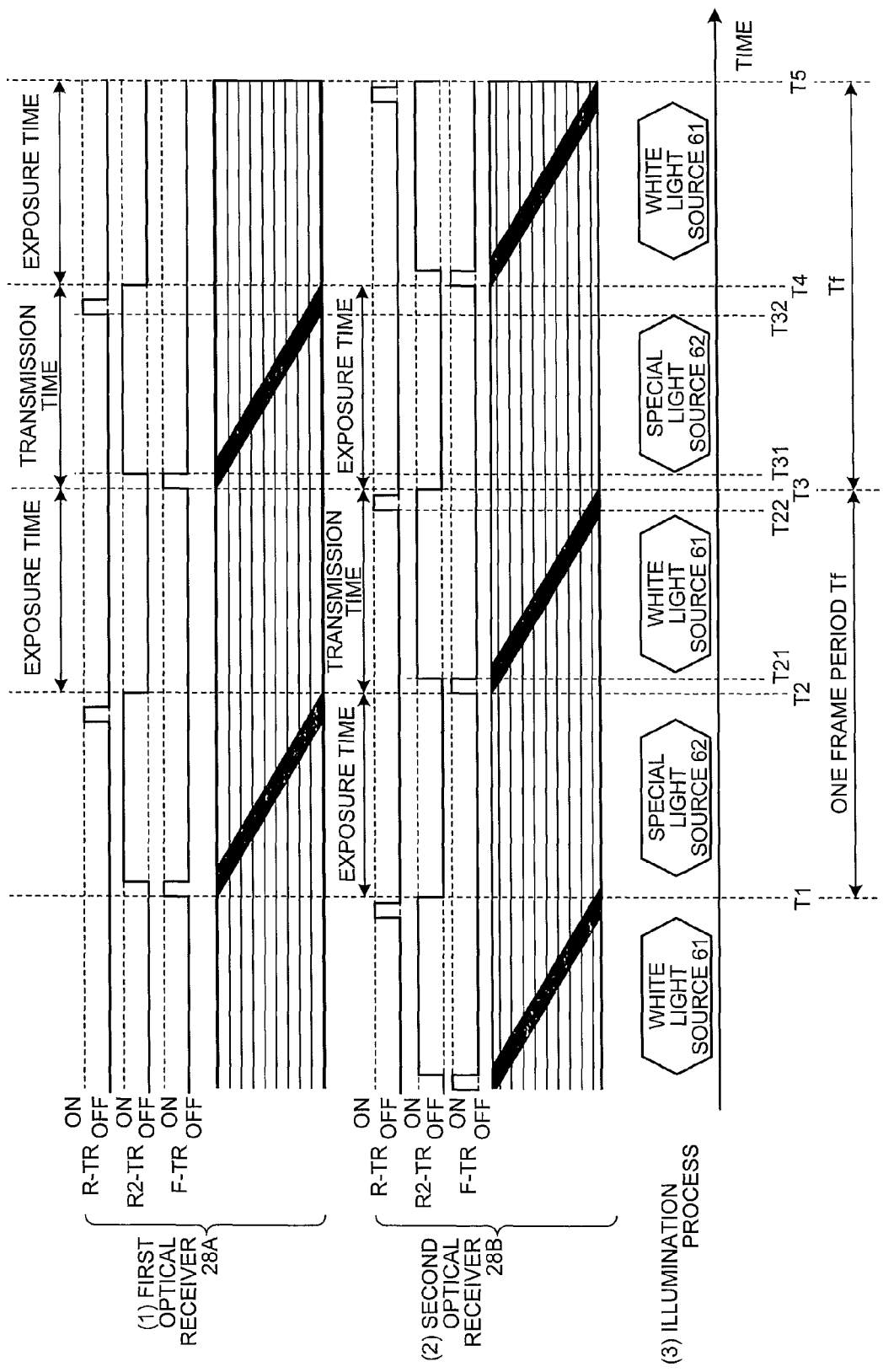
FIG. 16 is a diagram that includes timing charts for on/off control of transistors illustrated in FIG. 15.

As illustrated in FIG. 16, under the control of the tuning unit 81, in a first half period (an interval between time T1 and time T2) acquired by dividing one frame period Tf into two, the specialized light source 62 performs an illumination process, and, in correspondence with this, the second optical receiver 28B performs an exposure process. More particularly, in all the unit pixels of the second optical receiver 28B, the first reset transistor R-TR, the second reset transistor R2-TR, and the transmission transistor F-TR are controlled to be turned off, and signal charge corresponding to the amount of incident light is accumulated in the photodiode PD. In addition, in a first half period thereof (between time T1 and time T2), the first optical receiver 28A performs a reading/transmitting process. The operation control of each transistor in the first optical receiver 28A will be described below.

Subsequently, in a second half period (between time T2 and time T3) acquired by dividing one frame period Tf into two, the white light source 61 performs an illumination process, and, in correspondence with this, the first optical receiver 28A performs an exposure process. More specifically, in all the unit pixels of the first optical receiver 28A, the first reset transistor R-TR, the second reset transistor R2-TR, and the transmission transistor F-TR are controlled to be turned off, and signal charge corresponding to the amount of incident light is accumulated in the photodiode PD.

In addition, in this second half period (between time T2 and time T3), the second optical receiver 28B performs a reading/transmitting process. More specifically, in the unit pixel of the second optical receiver 28B that is included in the line pair as a reading target, between time T2 and time T21, the transmission transistor F-TR is controlled to be turned on, and the signal charge of the photodiode PD is transmitted to the capacitor FD. Thereafter, between time T21 and time T3, in a line as a reading target, the selection transistors S-TR are sequentially turned on in the order of reading, and the pixel information of each line is sequentially output. In the unit pixel included in the line pair as the reading target, between time T21 and time T3, the transmission transistor F-TR is controlled to be turned off, and the second reset transistor R2-TR is controlled to be turned on, whereby the photodiode PD is reset. Then, between time T22 and time T3, the first reset transistor R-TR is controlled to be turned on, and the capacitor FD is reset.

Also in the next frame, similarly, in the first half period (between time T3 and time T4), the specialized light source 62 performs an illumination process, and, in correspondence with this, the second optical receiver 28B performs an exposure process. More specifically, in all the unit pixels of the second optical receiver 28B, the first rest transistor R-TR, the second reset transistor R2-TR, and the transmission transistor F-TR are controlled to be turned off, and signal charge corresponding to the amount of incident light is accumulated in the photodiode PD.

In addition, in the first half period thereof (between time T3 and time T4), the first optical receiver 28A performs a reading/transmitting process. More specifically, in the unit pixel of the first optical receiver 28A that is included in the line pair as a reading target, between time T3 and time T31, the transmission transistor F-TR is controlled to be turned on, and the signal charge of the photodiode PD is transmitted to the capacitor FD. Thereafter, between time T31 and time T4, in the line as a reading target, the selection transistors S-TR are sequentially turned on in the order of reading, and the pixel information of each line is sequentially output. In the unit pixel included in the line pair as the reading target, between time T31 and time T4, the transmission transistor F-TR is controlled to be turned off, and the second reset transistor R2-TR is controlled to be turned on, whereby the photodiode PD is reset. Then, between time T32 and time T4, the first reset transistor R-TR is controlled to be turned on, and the capacitor FD is reset.

Modified Example 1 of the Second Embodiment

Figure 17:
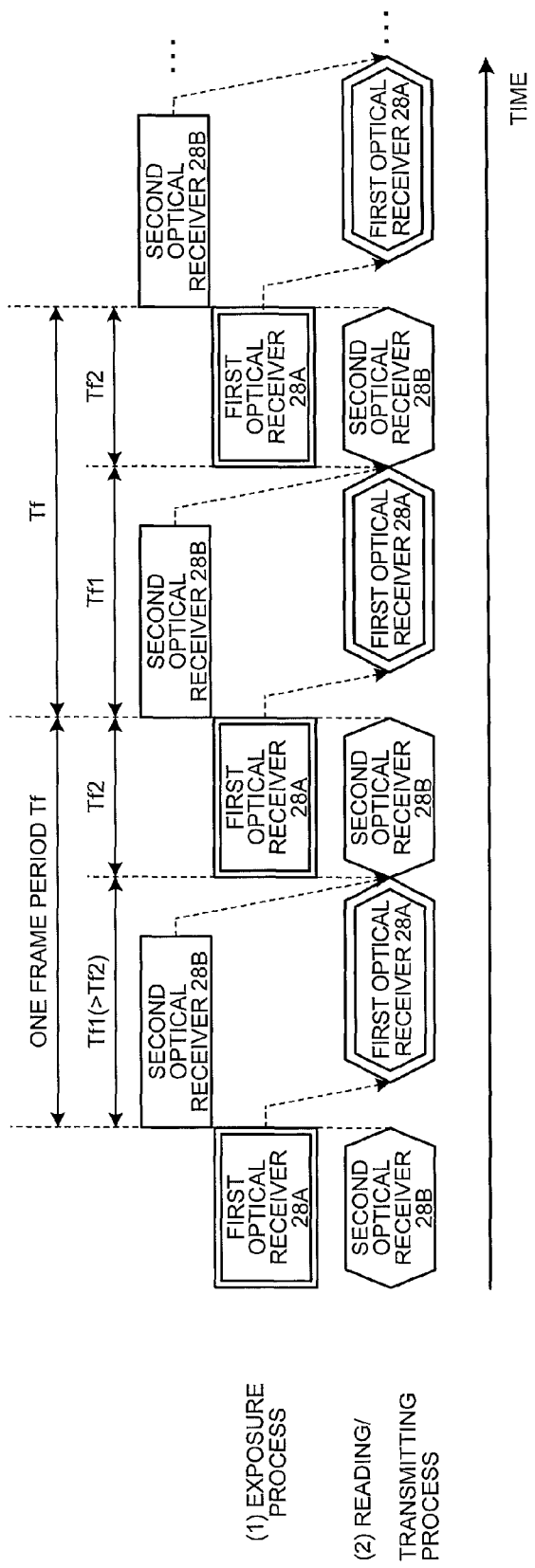
FIG. 17 is a diagram for describing exposure processes in the first and second optical receivers according to a Modified Example 1 of the second embodiment and processes of reading pixel information for the first and second optical receivers.

In the second embodiment, one frame period does not necessarily need to be divided into two periods of the same time length, and, as illustrated in FIG. 17, one frame period may be divided into periods of different time lengths from one another in accordance with the performance of the first and second optical receivers 28A and 28B. The tuning unit 81, for example, divides one frame period such that the first half period Tf1 is longer than the second half period Tf2. For example, one frame period is divided such that the first half period Tf1 is twice the second half period Tf2.

Then, in the first half period Tf1 of which the period is long, the tuning unit 81 allows the second optical receiver 28B to perform an exposure process. Since the second optical receiver 28B performs the exposure process for a long time, the amount of fluorescent light received in the second optical receiver 28B can increase, whereby the fluorescent light can be detected with a high sensitivity level. In addition, in the first half period Tf1, the tuning unit 81 allows the first optical receiver 28A to perform a reading/transmitting process.

Then, in the second half period Tf2 of which the period is short, the tuning unit 81 allows the second optical receiver 28B to perform a transmission process. In this case, the tuning unit 81 sets reading target pixels of the second optical receiver 28B such that the decimation amount is more than that of pixels of the reading target according to the second embodiment. In addition, in this second half period Tf2, the first optical receiver 28A is allowed to perform an exposure process. In a case where an image acquired by overlapping a color image according to white light and a fluorescent image, which is a specialized image, each other, it is sufficient that a portion emitting fluorescent light can be determined, and accordingly, the resolution of the fluorescent image is not particularly necessary, whereby an image can be appropriately generated even in a case where the decimation amount of pixels as reading targets is large.

This example is not limited to a case where one frame period is divided into the same periods, and, as in Modified Example 1 of the second embodiment, as long as a generation target image can be appropriately acquired, one frame period may be divided into periods of different time lengths from one another in accordance with the performance of the first and second optical receivers 28A and 28B.

Figure 18:
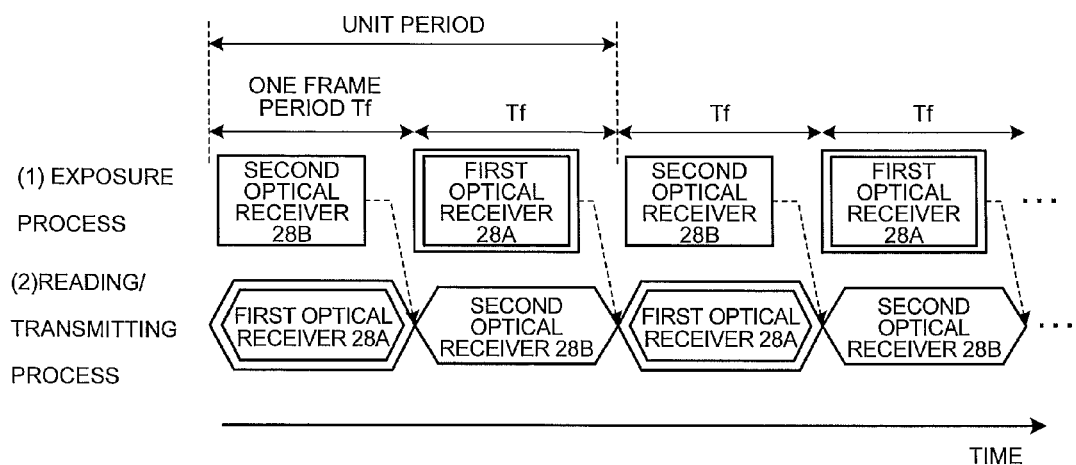
FIG. 18 is a diagram for describing another example of exposure processes in the first and second optical receivers according to the Modified Example 1 of the second embodiment and processes of reading pixel information for the first and second optical receivers.

A unit period for the division is not limited to one frame period. For example, as illustrated in FIG. 18, a two-frame period is set as a unit period, this unit period is divided into two, and, for each divided one frame period, the exposure processes in the first and second optical receivers 28A and 28B and the pixel information reading/transmitting processes for the first and second optical receivers 28A and 28B may be alternately performed. In other words, in one frame period of the first half, the tuning unit 81 allows the first optical receiver 28A to perform a reading/transmitting process and allows the second optical receiver 28B to perform an exposure process. Then, in two frame period of the second half, the tuning unit 81 allows the first optical receiver 28A to perform an exposure process and allows the second optical receiver 28B to perform a reading/transmitting process.

This embodiment is not limited to an endoscope system and may be applied to a television camera in which an imaging unit and a display monitor are connected to each other through a long cable. In addition, this embodiment may be applied to a photographing apparatus such as a digital camera, a digital single lens reflex camera, a digital video camera, or a camera-attached cellular phone.

As above, the imaging apparatus according to the present invention is useful for acquiring a plurality of kinds of images by employing a simple configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
   first and second imaging units, each of which is configured to output, as pixel information,
   an electric signal after photoelectric conversion from a pixel arbitrarily set as a reading target among a plurality of pixels for imaging;
   a reading circuit configured to read the pixel information from the pixel set as the reading target in each of the first and second imaging units;
   a control unit configured to control the reading circuit to read the pixel information alternately from the first and second imaging units to set the pixel as the reading target in each of the first and second imaging units, and
   configured to control timing of exposure processes in the first and second imaging units and timing of reading processes of the pixel information for the first and second imaging units by the reading circuit, to be correlated with one another;
   a transmission cable configured to transmit the pixel information read from each of the first and second imaging units through a same transmission path; and
   an image processing unit that generates an image based on the pixel information transmitted by the transmission cable
   wherein the plurality of pixels are two-dimensionally arranged in a matrix pattern, and wherein the control unit controls the reading circuit to read the pixel information of horizontal lines alternately from the first and second imaging units at a specified interval of lines to set the pixel as the reading target in each of the first and second imaging units.

2. The imaging apparatus according to claim 1 wherein the first and second imaging units have same imaging characteristics.

3. The imaging apparatus according to claim 1 wherein the first and second imaging units have different imaging characteristics from one another.

4. The imaging apparatus according to claim 3, wherein the first imaging unit has characteristics for capturing a color image, and the second imaging unit has characteristics for capturing a monochrome image.

5. The imaging apparatus according to claim 4, wherein the pixel information includes a luminance value, and wherein the control unit causes the reading circuit to add luminance values of pixels within a block in which a specified number of pixels are included and to output a resultant value as a luminance value of the pixels of the second imaging unit.

6. The imaging apparatus according to claim 1, wherein the control unit divides a unit of time into periods and causes the exposure processes in the first and second imaging units and the reading processes of the pixel information for the first and second imaging units by the reading circuit to be alternately performed in the divided periods.

7. The imaging apparatus according to claim 6, wherein the control unit divides the unit of time into periods having different time lengths from one another in accordance with characteristics of the first and second imaging units.

8. The imaging apparatus according to claim 6, wherein the plurality of pixels are two-dimensionally arranged vertically and horizontally, and wherein the control unit controls the reading circuit to read the pixel information of one horizontal line at a specified interval of lines from at least one of the first and second imaging units to set the pixel as the reading target in each of the first and second imaging units.

9. The imaging apparatus according to claim 6, wherein the unit of time is time required for the exposure process in the first imaging unit and a process of reading all the pixels of the first imaging unit.

10. The imaging apparatus according to claim 1, further comprising a converter that converts the pixel information read by the reading circuit from parallel to serial and outputs the converted pixel information to the transmission cable.

11. The imaging apparatus according to claim 1, wherein the image processing unit generates two images corresponding to the first and second imaging units, respectively, based on the pixel information alternately read from the first and second imaging units by the reading circuit.

12. The imaging apparatus according to claim 1, wherein the image processing unit generates one image using the pixel information alternately read from the first and second imaging units by the reading circuit.

13. The imaging apparatus according to claim 1, wherein the imaging apparatus is an endoscope apparatus comprising: a distal end portion that includes the first imaging unit, the second imaging unit, the reading circuit, and the control unit, and is configured to be introduced into an inside of a subject; and a signal processing device that includes the image processing unit and a display unit configured to display the image generated by the image processing unit and is connected to the distal end portion through the transmission cable.

* * * * *